(12) United States Patent
Zhi

(10) Patent No.: US 9,994,600 B2
(45) Date of Patent: Jun. 12, 2018

(54) PRODRUG COMPOUNDS AND USES THEROF

(71) Applicant: Ligand Pharmaceuticals, Inc., San Diego, CA (US)

(72) Inventor: Lin Zhi, San Diego, CA (US)

(73) Assignee: Ligand Pharmaceuticals, Inc., San Diego, CA (US)

(*) Notice: Subject to any disclaimer, the term of this patent is extended or adjusted under 35 U.S.C. 154(b) by 0 days. days.

(21) Appl. No.: 15/323,080

(22) PCT Filed: Jun. 26, 2015

(86) PCT No.: PCT/US2015/038044
§ 371 (c)(1),
(2) Date: Dec. 29, 2016

(87) PCT Pub. No.: WO2016/003812
PCT Pub. Date: Jan. 7, 2016

(65) Prior Publication Data
US 2017/0158725 A1    Jun. 8, 2017

Related U.S. Application Data

(60) Provisional application No. 62/020,044, filed on Jul. 2, 2014, provisional application No. 62/152,341, filed on Apr. 24, 2015.

(51) Int. Cl.
*A61K 31/663* (2006.01)
*C07F 9/6571* (2006.01)

(52) U.S. Cl.
CPC ...... *C07F 9/657181* (2013.01); *A61K 31/663* (2013.01); *C07F 9/657163* (2013.01)

(58) Field of Classification Search
CPC ......... C07F 9/657181; C07F 9/657163; A61K 31/663
See application file for complete search history.

(56) References Cited

U.S. PATENT DOCUMENTS

| | | | |
|---|---|---|---|
| 3,018,302 A | 1/1962 | Arnold et al. | |
| 3,116,282 A | 12/1963 | Hunter | |
| 3,328,388 A | 6/1967 | Shen et al. | |
| 3,404,178 A | 10/1968 | Roy | |
| 3,796,700 A | 3/1974 | Yoshioka et al. | |
| 4,255,566 A | 3/1981 | Carrico et al. | |
| 4,318,982 A | 3/1982 | Hornby et al. | |
| 4,340,668 A | 7/1982 | Hornby et al. | |
| 4,376,165 A | 3/1983 | Hornby et al. | |
| 4,440,740 A | 4/1984 | Fix et al. | |
| 4,447,529 A | 5/1984 | Greenquist et al. | |
| 4,537,772 A | 8/1985 | Alexander et al. | |
| 4,621,077 A | 11/1986 | Rosini et al. | |
| 4,659,825 A | 4/1987 | Holy et al. | |
| 4,692,441 A | 9/1987 | Alexander et al. | |
| 4,705,651 A | 11/1987 | Staibano | |
| 4,724,232 A | 2/1988 | Rideout et al. | |
| 4,724,233 A | 2/1988 | DeClercq et al. | |
| 4,729,989 A | 3/1988 | Alexander et al. | |
| 4,731,360 A | 3/1988 | Alexander et al. | |
| 4,749,694 A | 6/1988 | Fix et al. | |
| 4,757,141 A | 7/1988 | Fung et al. | |
| 4,777,163 A | 10/1988 | Bosies et al. | |
| 4,804,655 A | 2/1989 | Müller et al. | |
| 4,808,716 A | 2/1989 | Holy et al. | |
| 4,822,773 A | 4/1989 | Alexander et al. | |
| 4,835,138 A | 5/1989 | Alexander et al. | |
| 4,839,466 A | 6/1989 | Saltiel | |
| 4,847,298 A | 7/1989 | Alexander et al. | |
| 4,861,759 A | 8/1989 | Mitsuya et al. | |
| 4,879,277 A | 11/1989 | Mitsuya et al. | |
| 4,882,142 A | 11/1989 | Simon et al. | |
| 4,898,724 A | 2/1990 | Simon et al. | |
| 4,939,130 A | 7/1990 | Jaeggi et al. | |
| 4,952,575 A | 8/1990 | Sauerbier et al. | |
| 4,952,740 A | 8/1990 | Juge et al. | |
| 4,963,525 A | 10/1990 | Alexander et al. | |
| 4,963,556 A | 10/1990 | Alexander et al. | |
| 4,973,579 A | 11/1990 | Alexander et al. | |
| 5,034,394 A | 7/1991 | Daluge | |
| 5,047,533 A | 9/1991 | Reist et al. | |
| 5,077,280 A | 12/1991 | Sommadossi et al. | |
| 5,089,500 A | 2/1992 | Daluge | |
| 5,118,672 A | 6/1992 | Schinazi et al. | |
| 5,130,303 A | 7/1992 | Akiyama et al. | |
| 5,130,427 A | 7/1992 | Alexander et al. | |
| 5,142,051 A | 8/1992 | Holy et al. | |

(Continued)

FOREIGN PATENT DOCUMENTS

| | | |
|---|---|---|
| CH | 492 738 | 6/1970 |
| DE | 1693219 A | 9/1970 |

(Continued)

OTHER PUBLICATIONS

Shoshani et al., 274(49) J. Bio. Chem. 34735-34741 (1999) (CAS Abtract).*
Burrows et al., "Synthesis, Characterization, and Electrochemistry of a Series of Iron(II) Complexes Containing Self-Assembled 1,5-Diaza-3,7-diphosphabicyclo[3.3.1]nonane Ligands", Inorg Chem. (2009) 48: 9924-9935.
De Waziers et al., "Cytochrome P 450 isoenzymes, epoxide hydrolase and glutathione transferases in rat and human hepatic nd extrahiepatic tissues", J Pharm Exp Ther. (1990) 253(1): 387-394.
Erion et al., "Liver-Targeted Drug Delivery Using HepDirect Prodrugs" J Pharmacol Exper Ther. (2005) 312(2): 554-560.
Hammer et al., "Phosphorylation of the Nuclear Receptor SF-1 Modulates Cofactor Recruitment: Integration of Hormone Signaling in Reproduction and Stress", Mol Cell (1999) 3: 521-526.

(Continued)

*Primary Examiner* — Timothy R Rozof
(74) *Attorney, Agent, or Firm* — Knobbe, Martens, Olson & Bear, LLP

(57) ABSTRACT

Provided herein are cyclic phosphorus-containing prodrug compounds, their preparation and their uses, such as treating diseases via modulating molecular targets in the liver.

19 Claims, No Drawings

(56) References Cited

U.S. PATENT DOCUMENTS

| | | |
|---|---|---|
| 5,153,183 A | 10/1992 | Kawabe et al. |
| 5,157,027 A | 10/1992 | Biller et al. |
| 5,159,067 A | 10/1992 | Schinazi et al. |
| 5,204,355 A | 4/1993 | Zsadon et al. |
| 5,210,085 A | 5/1993 | Liotta et al. |
| 5,212,304 A | 5/1993 | Fung et al. |
| 5,240,946 A | 8/1993 | Kinney et al. |
| 5,246,937 A | 9/1993 | Hamden et al. |
| 5,258,538 A | 11/1993 | Fung et al. |
| 5,366,965 A | 11/1994 | Strein |
| 5,437,772 A | 8/1995 | De Castro et al. |
| 5,464,748 A | 11/1995 | Sommadossi et al. |
| 5,480,875 A | 1/1996 | Isomura et al. |
| 5,514,798 A | 5/1996 | Bischofberger et al. |
| 5,532,225 A | 7/1996 | Reist et al. |
| 5,567,689 A | 10/1996 | Sommadossi et al. |
| 5,583,122 A | 12/1996 | Benedict et al. |
| 5,599,686 A | 2/1997 | DeFeo-Jones et al. |
| 5,627,164 A | 5/1997 | Glazier |
| 5,658,889 A | 8/1997 | Gruber et al. |
| 5,663,159 A | 9/1997 | Starrett, Jr. et al. |
| 5,665,386 A | 9/1997 | Benet et al. |
| 5,681,590 A | 10/1997 | Bechard et al. |
| 5,686,629 A | 11/1997 | Bischofberger et al. |
| 5,716,928 A | 2/1998 | Benet et al. |
| 5,721,219 A | 2/1998 | Ingall et al. |
| 5,723,449 A | 3/1998 | Sommadossi et al. |
| 5,750,493 A | 5/1998 | Sommadossi et al. |
| 5,767,097 A | 6/1998 | Tam |
| 5,789,608 A | 8/1998 | Glazier |
| 5,814,639 A | 9/1998 | Liotta et al. |
| 5,840,716 A | 11/1998 | Ubasawa et al. |
| 5,854,231 A | 12/1998 | Camden |
| 5,866,679 A | 2/1999 | DeFeo-Jones et al. |
| 5,866,684 A | 2/1999 | Attwood et al. |
| 5,869,467 A | 2/1999 | Holy et al. |
| 5,914,331 A | 6/1999 | Liotta et al. |
| 5,948,750 A | 9/1999 | Garsky et al. |
| 5,962,440 A | 10/1999 | Sulsky |
| 5,962,522 A | 10/1999 | Wacher et al. |
| 5,990,093 A | 11/1999 | Schinazi et al. |
| 6,004,927 A | 12/1999 | Benet et al. |
| 6,028,054 A | 2/2000 | Benet et al. |
| 6,037,335 A | 3/2000 | Takashima et al. |
| 6,045,638 A | 4/2000 | Lundstrom |
| 6,054,587 A | 4/2000 | Reddy et al. |
| 6,110,903 A | 8/2000 | Kasibhatla et al. |
| 6,117,873 A | 9/2000 | Acklin et al. |
| 6,121,234 A | 9/2000 | Benet et al. |
| 6,128,582 A | 10/2000 | Wilson et al. |
| 6,130,326 A | 10/2000 | Ramasamy et al. |
| 6,130,504 A | 10/2000 | Nakayama et al. |
| 6,143,715 A | 11/2000 | Llinas-Brunet et al. |
| 6,143,864 A | 11/2000 | DeFeo-Jones et al. |
| 6,177,404 B1 | 1/2001 | DeFeo-Jones et al. |
| 6,180,666 B1 | 1/2001 | Wacher et al. |
| 6,194,390 B1 | 2/2001 | Lori et al. |
| 6,194,391 B1 | 2/2001 | Schinazi et al. |
| 6,211,201 B1 | 4/2001 | Granger et al. |
| 6,245,749 B1 | 6/2001 | Schinazi et al. |
| 6,284,748 B1 | 9/2001 | Dang et al. |
| 6,294,672 B1 | 9/2001 | Reddy et al. |
| 6,312,662 B1 | 11/2001 | Erion et al. |
| 6,348,587 B1 | 2/2002 | Schinazi et al. |
| 6,372,883 B1 | 4/2002 | Attwood et al. |
| 6,391,305 B1 | 5/2002 | Feng et al. |
| 6,395,716 B1 | 5/2002 | Gosselin et al. |
| 6,395,763 B1 | 5/2002 | Stamos et al. |
| 6,399,773 B1 | 6/2002 | Liu et al. |
| 6,399,782 B1 | 6/2002 | Kasibhatla et al. |
| 6,403,566 B1 | 6/2002 | Wang |
| 6,407,077 B1 | 6/2002 | Gosselin et al. |
| 6,423,695 B1 | 7/2002 | Tam et al. |
| 6,444,652 B1 | 9/2002 | Gosselin et al. |
| 6,448,281 B1 | 9/2002 | Beaulieu et al. |
| 6,455,508 B1 | 9/2002 | Ramasamy et al. |
| 6,458,773 B1 | 10/2002 | Gosselin et al. |
| 6,486,204 B2 | 11/2002 | Waldstreicher et al. |
| 6,489,476 B1 | 12/2002 | Dang et al. |
| 6,495,677 B1 | 12/2002 | Ramasamy et al. |
| 6,518,253 B1 | 2/2003 | Tam |
| 6,525,033 B1 | 2/2003 | Schinazi et al. |
| 6,545,007 B2 | 4/2003 | Sommadossi et al. |
| 6,566,344 B1 | 5/2003 | Gosselin et al. |
| 6,569,837 B1 | 5/2003 | Gosselin et al. |
| 6,596,700 B2 | 7/2003 | Sommadossi et al. |
| 6,602,664 B2 | 8/2003 | Schinazi et al. |
| 6,608,027 B1 | 8/2003 | Tsantrizos et al. |
| 6,608,067 B1 | 8/2003 | Tung et al. |
| 6,613,896 B1 | 9/2003 | Ramasamy et al. |
| 6,635,636 B1 | 10/2003 | Artico et al. |
| 6,653,295 B2 | 11/2003 | Glunz et al. |
| 6,727,267 B2 | 4/2004 | Jaen et al. |
| 6,752,981 B1 | 6/2004 | Erion et al. |
| 6,756,360 B1 | 6/2004 | Erion et al. |
| 6,767,991 B1 | 7/2004 | Llinas-Brunet et al. |
| 6,777,395 B2 | 8/2004 | Bhat et al. |
| 6,784,166 B2 | 8/2004 | Devos et al. |
| 6,809,101 B2 | 10/2004 | Fujishita et al. |
| 6,846,810 B2 | 1/2005 | Armstrong et al. |
| 6,864,244 B2 | 3/2005 | Connolly et al. |
| 6,867,284 B1 | 3/2005 | Matassa et al. |
| 6,911,428 B2 | 6/2005 | Zhu et al. |
| 6,914,054 B2 | 7/2005 | Sommadossi et al. |
| 6,946,115 B2 | 9/2005 | Erion et al. |
| 6,994,959 B1 | 2/2006 | Tam |
| 7,081,449 B2 | 7/2006 | Pietrzkowski et al. |
| 7,091,209 B2 | 8/2006 | Gardelli et al. |
| 7,094,768 B2 | 8/2006 | Roberts et al. |
| 7,094,770 B2 | 8/2006 | Watanabe et al. |
| 7,105,493 B2 | 9/2006 | Sommadossi et al. |
| 7,148,349 B2 | 12/2006 | Reddy et al. |
| 7,151,092 B2 | 12/2006 | Boyer et al. |
| 7,169,766 B2 | 1/2007 | Sommadossi et al. |
| 7,193,081 B2 | 3/2007 | Kopcho et al. |
| 7,205,404 B1 | 4/2007 | Erion et al. |
| 7,214,668 B2 | 5/2007 | Erion et al. |
| 7,261,704 B2 | 8/2007 | Tachikawa et al. |
| 7,303,739 B2 | 12/2007 | Erion et al. |
| 7,351,399 B2 | 4/2008 | Erion et al. |
| 7,429,572 B2 | 9/2008 | Clark |
| 7,491,794 B2 | 2/2009 | Blatt et al. |
| 7,498,320 B2 | 3/2009 | Reddy et al. |
| 7,553,826 B2 | 6/2009 | Boyer et al. |
| 7,582,758 B2 | 9/2009 | Martin |
| 7,608,600 B2 | 10/2009 | Storer et al. |
| 7,666,855 B2 | 2/2010 | Reddy et al. |
| 7,816,345 B2 | 10/2010 | Erion et al. |
| 8,063,025 B2 | 11/2011 | Hecker et al. |
| 8,080,536 B2 | 12/2011 | Erion et al. |
| 8,664,195 B2 | 3/2014 | Erion et al. |
| 9,326,991 B2 | 5/2016 | Zhi et al. |
| 2001/0041713 A1 | 11/2001 | Waldstreicher et al. |
| 2002/0115596 A1 | 8/2002 | Garsky et al. |
| 2002/0120130 A1 | 8/2002 | Gosselin et al. |
| 2002/0147160 A1 | 10/2002 | Bhat et al. |
| 2002/0187945 A1 | 12/2002 | Tam |
| 2002/0193415 A1 | 12/2002 | LaColla et al. |
| 2003/0008841 A1 | 1/2003 | Devos et al. |
| 2003/0050229 A1 | 3/2003 | Sommadossi et al. |
| 2003/0050320 A1 | 3/2003 | Hashimoto et al. |
| 2003/0060400 A1 | 3/2003 | LaColla et al. |
| 2003/0083306 A1 | 5/2003 | Imbach et al. |
| 2003/0087873 A1 | 5/2003 | Stuyver et al. |
| 2003/0229225 A1 | 12/2003 | Reddy et al. |
| 2003/0232760 A1 | 12/2003 | Garsky et al. |
| 2004/0006002 A1 | 1/2004 | Sommadossi et al. |
| 2004/0006007 A1 | 1/2004 | Grosselin et al. |
| 2004/0014696 A1 | 1/2004 | Lau et al. |
| 2004/0019232 A1 | 1/2004 | Hostetler et al. |
| 2004/0063651 A1 | 4/2004 | Morioka et al. |
| 2004/0063658 A1 | 4/2004 | Roberts et al. |
| 2004/0067877 A1 | 4/2004 | Schinazi et al. |
| 2004/0077563 A1 | 4/2004 | Lau et al. |

(56) References Cited

U.S. PATENT DOCUMENTS

| | | |
|---|---|---|
| 2004/0147464 A1 | 7/2004 | Roberts et al. |
| 2004/0266723 A1 | 12/2004 | Otto et al. |
| 2005/0031588 A1 | 2/2005 | Sommadossi et al. |
| 2005/0054645 A1 | 3/2005 | Miyazaki et al. |
| 2005/0075309 A1 | 4/2005 | Storer et al. |
| 2005/0090463 A1 | 4/2005 | Roberts et al. |
| 2005/0101775 A1 | 5/2005 | Erion et al. |
| 2005/0101776 A1 | 5/2005 | Gosselin et al. |
| 2005/0107312 A1 | 5/2005 | Keicher et al. |
| 2005/0182252 A1 | 8/2005 | Reddy et al. |
| 2005/0282782 A1 | 12/2005 | Martin |
| 2006/0030545 A1 | 2/2006 | Cheng et al. |
| 2006/0046981 A1 | 3/2006 | Shibata |
| 2006/0234962 A1 | 10/2006 | Olsen et al. |
| 2007/0213588 A1 | 1/2007 | Reddy et al. |
| 2007/0032448 A1 | 2/2007 | Hong et al. |
| 2007/0060498 A1 | 3/2007 | Gosselin et al. |
| 2007/0179114 A1 | 8/2007 | Erion et al. |
| 2007/0183706 A1 | 8/2007 | Huang |
| 2007/0203339 A1 | 8/2007 | Kopcho et al. |
| 2008/0009533 A1 | 1/2008 | Tino et al. |
| 2008/0125605 A1 | 5/2008 | Erion et al. |
| 2009/0209481 A1 | 8/2009 | Hecker et al. |
| 2010/0305060 A1 | 12/2010 | Hecker et al. |
| 2011/0009356 A1 | 1/2011 | Erion et al. |
| 2011/0098251 A1 | 4/2011 | Ebetino et al. |
| 2012/0039845 A1 | 2/2012 | Hecker et al. |
| 2012/0093729 A1 | 4/2012 | Erion et al. |
| 2013/0310395 A1 | 11/2013 | Dodd et al. |
| 2014/0142052 A1 | 5/2014 | Lehn et al. |
| 2017/0056429 A1 | 3/2017 | Zhi |

FOREIGN PATENT DOCUMENTS

| | | |
|---|---|---|
| EP | 0002062 A | 5/1979 |
| EP | 0072531 A | 2/1983 |
| EP | 0072987 | 3/1983 |
| EP | 0158057 A | 10/1985 |
| EP | 0161955 | 11/1985 |
| EP | 0180276 A1 | 5/1986 |
| EP | 0261283 A | 3/1988 |
| EP | 0338372 A2 | 10/1989 |
| EP | 0353692 B1 | 2/1990 |
| EP | 0481214 A | 4/1992 |
| EP | 0632048 | 1/1995 |
| GB | 987378 | 3/1965 |
| GB | 2266525 A | 11/1993 |
| GB | 2266527 A | 11/1993 |
| JP | 62-195392 A2 | 8/1987 |
| JP | 62-249996 A2 | 10/1987 |
| JP | H09241284 A | 9/1997 |
| WO | WO 1990/008155 | 7/1990 |
| WO | WO 1990/010636 | 9/1990 |
| WO | WO 1993/019075 | 9/1993 |
| WO | WO 1995/07287 | 3/1995 |
| WO | WO 1995/007920 | 3/1995 |
| WO | WO 1996/001267 | 1/1996 |
| WO | WO 1997/003679 | 2/1997 |
| WO | WO 1997/022614 | 6/1997 |
| WO | WO 1997/049717 | 12/1997 |
| WO | WO 1998/008458 | 3/1998 |
| WO | WO 1998/009668 | 3/1998 |
| WO | WO 1998/038888 | 9/1998 |
| WO | WO 1998/039342 | 9/1998 |
| WO | WO 1998/039343 | 9/1998 |
| WO | WO 1998/039344 | 9/1998 |
| WO | WO 1998/046630 | 10/1998 |
| WO | WO 1999/004774 | 2/1999 |
| WO | WO 1999/004908 | 2/1999 |
| WO | WO 1999/036074 | 7/1999 |
| WO | WO 99/45016 | 9/1999 |
| WO | WO 1999/047549 | 9/1999 |
| WO | WO 2000/003998 | 1/2000 |
| WO | WO 2000/009531 | 2/2000 |
| WO | WO 2000/014095 | 3/2000 |
| WO | WO 2000/038666 | 7/2000 |
| WO | WO 2000/052015 | 9/2000 |
| WO | WO 2001/027114 | 4/2001 |
| WO | WO 2001/039724 | 6/2001 |
| WO | WO 2001/045509 | 6/2001 |
| WO | WO 2001/045642 | 6/2001 |
| WO | WO 2001/092282 | 12/2001 |
| WO | WO 2001/093383 | 12/2001 |
| WO | WO 2002/000673 | 1/2002 |
| WO | WO 2002/008241 | 1/2002 |
| WO | WO 2002/015904 | 2/2002 |
| WO | WO 2002/083126 | 10/2002 |
| WO | WO 2003/014821 | 2/2003 |
| WO | WO 2003/014822 | 2/2003 |
| WO | WO 2003/026589 | 4/2003 |
| WO | WO 2003/026675 | 4/2003 |
| WO | WO 2003/034690 | 4/2003 |
| WO | WO 2003/034709 | 4/2003 |
| WO | WO 2003/037908 | 5/2003 |
| WO | WO 2003/051881 | 6/2003 |
| WO | WO 2003/051896 | 6/2003 |
| WO | WO 2003/051897 | 6/2003 |
| WO | WO 2003/051898 | 6/2003 |
| WO | WO 2003/051899 | 6/2003 |
| WO | WO 2003/052053 | 6/2003 |
| WO | WO 2003/068244 | 8/2003 |
| WO | WO 2004/002422 | 1/2004 |
| WO | WO 2004/002999 | 1/2004 |
| WO | WO 2004/003000 | 1/2004 |
| WO | WO 2006/033709 | 3/2006 |
| WO | WO 2007/020193 | 2/2007 |
| WO | WO 2009/073506 | 6/2009 |

OTHER PUBLICATIONS

Hartung et al., "1,5-Diphosphabicycle[3.3.1]nonane 1,5-Disulfide", Acta Cryst. (1988) C44: 1438-1440.

Koh et al., "Design, Synthesis, and Antiviral Activity of Adenosine 5'-Phosphonate Analogues as Chain Terminators against Hepatitis C Virus", J Med Chem. (2005) 48(8): 2867-2875.

PubChem. SID 22395163; online Feb. 23, 2007; NIH U.S. National Library of Medicine [retrieved on Aug. 25, 2015]; 9 pages.

Rautio et al., "Prodrugs: design and clinical applications", Nature Rev Drug Disc. (2008) 7: 255-270.

Sinicrope et al., "Modulation of P-glycoprotein-mediated Drug Transport by Alterations in Lipid Fluidity of Rat Liver Canalicular Membrane Vescicles", J Biol Chem. (1992) 267(36): 24995-25002.

Zhou et al., "IDX184, A liver-targeted Nucleotide HCV Polymerase Inhibitor: Results of a First-in-Man Safety and Pharmacokinetic Study", Poster No. 966; 44th Annual Meeting European Association for the Study of the Liver (EASL); Copenhagen, Denmark Apr. 22-26, 2009; 1 page.

International Search Report and Written Opinion dated Dec. 10, 2015 for corresponding Application No. PCT/US2015/038044.

Alarcon R.A., "Studies on the In Vivo Formation of Acrolein: 3-Hydroxy-propylmercapturic Acid as an Index of Cyclophosphamide (NSC-26271) Activation," Cancer Treat Rep. (1976) 60(4): 327-335.

Aleksiuk et al., "Proximal Intraannular Modifictions of Calix[4]arene via its Spirodienone Derivative", J Chem Soc Chem Commun. (1993) 1: 11-13.

Alexakis et al., "Reactivity and Diastereoselectivity of Grignard Reagents toward the Hydrazone Functionality in Toluene Solvent," J Org Chem. (1992) 57(17): 4563-4565.

Alexander et al., "Preparation of 9-(2-Phosphonomethoxyethyl) Adenine Esters as Potential Prodrugs," Collect. Czech. Chem. Commun., (1994) 59: 1853-1869.

Allison et al., "Immunosuppressive and other anti-rheumatic activities of mycophenolate mofetil", Agents Actions *Suppl.* (1993) 44: 165-188.

Amin et al "1-Hydroxy-3-(methylpentylamino)-propylidene-1, 1-bisphosphonic Acid as a Potent Inhibitor of Squalene Synthase," Arznemittelforschung. (1996) 46(8): 759-762.

Anderson et al., "2-Chloro-4(R),5(R)-dimethyl-2-oxo-1,3,2-dioxphospholane, a new chiral derivatizing agent," J Org Chem (1984) 49(7): 1304-1305.

(56) References Cited

OTHER PUBLICATIONS

Anderson et al., "Cyclophosphamide and 4-Hydroxycyclophosphamide/Aldophosphamide Kinetics in Patients Receiving High-Dose Cyclophosphamide Chemotherapy," Clin Cancer Res. (1996) 2: 1481-1487.

Annaert et al., "Transport, Uptake, and Metabolism of the Bis(pivaloyloxymethyl)-Ester Prodrug of 9(2-Phosphonylmethoxyethyl) Adenine in an In Vitro Cell Culture System of the Intestinal Mucosa (Caco-2)," Pharm Res. (1997) 14(4): 492-496.

Anzenbacherova, et al., "In Vivo Study of the Effect of Antiviral Acyclic Nucleotide Phosphonate(R)-9-[2(phosphonomethoxy)propyl]adenine (PMPA, tenofovir) and Its Prodrug Tenofovir Disoproxil Fumarate on Rat Microsomal Cytochrome P450," Physiol Res. (2008) 57: 761-767.

Arnér et al., "Mammalian Deoxyribonucleoside Kinases," PharmaC Ther. (1995) 67(2): 155-186.

Arnold et al., "Über Beziehungen zwischen chemischer Konstitution und cancerotoxischer Wirkung in der Reihe der Phosphamidester des Bis—(β-chloräthyl)—amins," Konstitution und Wirkung, (1961) 11(2a): 143-158.

Aso et al., "Synthesis of a new class of spin-labeled purine ribonucleosides and development of novel nucleophilic reaction to form 2,6,8-trifunctionalized purine derivatives," J Chem Soc Perkins Trans. (2000) 2: 1637-1638.

Atiq et al. "Treatment of Unresectable Primary Liver cancer With Intrahepatic Fluorodeoxyuridine and Mitomycin C Through an Implantable Pump," Cancer (1992) 69: 920-924.

Attanasi et al., "Syntheis of some phosphorus derivatives of cardanol", Phosphor Sulfur (1988) 35(1-2): 63-65.

Auberson et al., "N-Phosphoalkyl-5-Aminomethylquinoxaline-2,3-Diones: in Vivo Active Ampa and NMDA(Glycine) Antagonist," Bioorg Med Chem Lttr. (1999) 9(2): 249-254.

Ayral-Kaloustian et al., "Synthesis of Partially-Protected D-Frutofuranoses and D-Fructose-6-Phosphates", Carbohydrate Res. (1991) 214: 187-192.

Baker et al., "Microtiter Plate Assay for the Measurement of Glutathione and Gluthione Disulfide in Large Numbers of Biological Samples," Anal Biochem. (1990) 190: 360-365.

Ballatore et al., "Carboxylic Acid (Bio)Isosteres in Drug Design", Chem Med Chem (2013) 8: 385-395.

Balthazor et al. "Nickel-Catalyzed Arbuzov Reaction: Mechanistic Observation," J Org Chem. (1980) 45: 5425-5426.

Balzarini et al., "5-Phosphoribosyl 1-Pyrophossphate Synthetase converts the acyclic nucleoside Phosphonates 9-(3-Hydroxy-2-phosphonylmethoxypropyl)adenine and 9-(2-Phosphonyl-methoxyethyl)adenine directly to their antivirally active Diposphate derivatives", J Biol Chem. (1991) 266(14): 8686-8689.

Balzarini et al., "Activity of the (R)-enantiomers of 9-(2-phosphonylmethoxypropyl)-Adenine and 9-(2-phosphonylmethoxypropyl)-2,6-diamiopurine against Human Immunodeficiency Virus in Different Human Cell Systems" Biochem Biophys Res Commun. (1996) 219: 337-341.

Banker, G.S. et al, "Modern Pharmaceutics, 3ed.", Marcel Dekker, New York, 1996, pp. 451 and 596.

Barluenga et al., "β-Substituted Organolithium Compounds. New Reagents for Synthesis," J Org Chem. (1979) 44(26): 4798-4801.

Barluenga et al., "Reduction of 1,3-Diimines. A New and General Method of Synthesis of gamma-Diamines, beta-Amino Ketones, and Derivatives with Two and Three Chiral Centers," J Org Chem. (1983) 48(13): 2255-2259.

Barluenga et al., "Stereoselective Synthesis of 1,3-Amino Alcohols and 1,3-Amino Ketones," J Org Chem. (1992) 57(4): 1219-1223.

Beaucage et al. "The Synthesis of Modified Oligonucleotides by the Phosphoramidite Approach and Their Applications," Tetrahed. (1993) 49(28): 6123-6194.

Bedford et al., "Synthesis of Water-Soluble Prodrugs of the Cytotoxic Agent Combretastatin A4," Bioorg Med Chem Lett. (1996) 6(2): 157-160.

Beigelman et al., "New Syntheses of 2'C-*Methylnucleosides* Starting from $_D$-Glucose and $_D$-Ribose," Carbohydrate Res. (1987) 166: 219-232.

Beilstein Registry 1028505, "2-phenoxy-6,6-diphenyl-[1,3,2]oxazaphosphinane 2-oxide", Beilstein Institute for Organic Chemistry, Frankfurt, Germany; Nov. 28, 1988, 2 pages.

Beilstein Registry 1083232, "2-phenoxy-4-phenyl-<1,3,2>diazaphosphinane", Beilstein Institute for Organic Chemistry, Frankfurt, Germany, Nov. 29, 1988; 1 page.

Beilstein Registry 1085700, "3-mehty1-2-phenoxy-6-phenyl-[1,3,2]diazaphosphinane 2-oxide", Beilstein Institute for Organic Chemistry, Frankfurt, Germany, entry date Nov. 29, 1988, in 1 page.

Beilstein Registry 6530655, "2-phenoxy-6,6-diphenyl-[1,3,2]oxazaphosphinane 2-oxide", Beilstein Institute for Organic Chemistry, Frankfurt, Germany, Apr. 18, 1994, 2 pages.

Beilstein Registry No. 3635189, "carboxy-phosphonic acid; sodium salt", Beilstein Institute for Organic Chemistry, Frankfurt, Germany, Feb. 26, 1991, 31 pages.

Benhamou et al., "Safety and efficacy of adefovir dipivoxil in patients co-infected with HIV-1 and lamivudine-resistant hepatitis B virus: an open-label pilot study," Lancet. (2001) 358(9283): 718-23.

Bentrude et al., "Stereo—and Regiochemistries of the Oxidations of 2-Methoxy-5-tert-butyl-1,3,2-dioxaphosphorinanes and the Cyclis Methyl 3'5'-Phosphite of Thymidine by $H_2O/I_2$ and $O_2/Aibn$ to P-Chiral Phosphates. $^{17}O$ NMR Assignment of Phosphorus Configuration to the Diasteromeric Thymidine Cyclic Methyl 3'5'-Monophosphates," J Am Chem Soc. (1989) 111: 3981-3987.

Bentrude et al. "Conformation of Saturated Six-Membered-Ring Phosphorus Heterocycles. 2-Aryl-1,3,2lambda$^5$-oxazapphosphorinanes" J Am Chem Soc. (1988) 110: 7119-7127.

Bentrude et al. "Conformations of Saturated Six-Membered-Ring Phosphorus Heterocycles Related to Cyclophosphamide. NMR, X-ray, and Infrared Studies of 2-Methoxy-2-oxo-1,3,2-oxazaphosphorinane and 2-Thio-1,3,2-oxazaphosphorinane" J Am Chem Soc. (1986) 108: 6696-6675.

Benzaria et al., "Synthesis, in Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability," J Med Chem. (1996) 39(25): 4958-4965.

Berry et al., "High-Yield Preparation of Isolated Rat Liver Parenchyman Cells," J Cell Biol. (1969) 43: 506-520.

Bertocchio et al., "Additions nucléophiles des cétones sur les fonctions éthyléiques activés," Bull. Soc. Chim. Fr, 1962, fasciclue 7, 307: 1809-1813.

Bespalov et al., "Prologation of morphine analgesia by competitive NMDA receptor antagonist D-CPPene (SDZ EAA 494) in rats," Euro J Pharmacol. (1998) 351: 299-305.

Bhatia et al., A new approach to the Synthesis of Ether Phospolipids. Etc. Tetra Lttrs. (1987) 28(3): 271-274.

Bhongle et al., "Expedient and High-Yield Synthesis of Alkylphosphonyl Dichlorides Under Mild, Neutral Conditions: Reaction of Bis(Trimethylsilyl) Alkyl Phosphonates with Oxalyl Chloride/Dimethylformamide," Synth Commun. (1987) 17(9-16): 1071-1076.

Bijsterbosch et al., "Disposition of the Acyclic Nucleoside Phosphonate (S)-9-(3-Hydroxy-2-Phosphonylmethoxypropyl) Adenine," Antimc Agt Chemother. (1998) 42(5): 1146-1150.

Bird et al., "Synthesis of Novel N-Phosphonoalkyl Dipeptide Inhibitors of Human Collagenase," J Med Chem. (1994) 73: 158-169.

Boddy et al., "Individual Variation in the Activation and Inactivation of Metabolic Pathways of Cyclophosphamide," J Nat Cancer Inst. (1992) 84(22): 744-748.

Borch et al.: "The Mechanism of Activation of 4-Hydroxycyclophosphamide," J Med Chem. (1987) 30: 427-431.

Borch et al., "Synthesis and Antitumor Properties of Activated Cyclophosphamide Analogues," J Med Chem. (1991) 34(10): 3044-3052.

Borch et al., "Synthesis, Activation and Cytotoxicity of Aldophosphamide Analogues," J Med Chem. (1991) 34(10): 3052-3058.

(56) References Cited

OTHER PUBLICATIONS

Boyd et al., "Synthesis and Antitumor Activity of Cyclophosphamide Analogues. 3. Preparation, Molecular Structure Determination, and Anticancer Screening of Racemic cis- and trans-4-Phenylcyclophosphamide," J Med Chem. (1980) 23(4): 372-375.
Boyer et al., "The Discovery of MB07133: A HepDirect® Prodrug of Cytarabine Monophosphate for the Treatment of Hepatocellular Carcinoma", Poster; Prospective, Boston, MA (May 2006); 1 page.
Boyer et al., "Synthesis and Characterization off a Novel Liver-Targeted Prodrug of Cytosine-1-beta-D-arabinofuranoside Monophosphate for the Treatment of Hepatocellular Carcinoma," J Med Chem (2006) 49: 7711-7720.
Braess et al. "Oral Cytarabine Ocfostate in Acute Myeloid Leukemia and non-Hodgkins's Lymphoma—Phase I/II Studies and Pharmacokinetics", Leukemia (1998) 12: 1618-1626.
Brain et al., "Modulation of P450-Dependent Ifosfamide Pharmacokinetics: a Better Understanding of Drug Activation In Vivo," British J Cancer 77(11): 1768-1776.
Brechbühler et al., "Die Reaktion von Carbonsäuren mit Acetalen des N,N-Dimethylformamids: eine Veresterungsmethode," Helvetica Chimica Acta (1965) 48(7): 1746-1771.
Brenna et al, "Affinity-Chromatography Purification of Alkaline Phosphatase from Calf Intestine," Biochem J., (1975) 151: 291-296.
Brill et al., "Arbuzov-like Dealkylation Reactions of Transition-Metal-Phosphite Complexes," Chem Rev (1984) 84(6): 577-585.
Brock et al., "Acrolein, the Causative Factor of Urotoxic Side-effects of Cyclophosphamide, Ifosfamide, Trofosfamide and Sufosfamide," Drug Res. (1979) 29(4): 659-661.
Bronson et al., "Synthesis and Antiviral Activity of Nucleotide Analogs Bearing the (S)-(3-hydroxy-2-phosphonylmethoxy)propyl Moiety Attached to Adenine, Guanine, and Cytosine," in *Nucleotide Analogues as Antiviral Agents*; (1989) Chapter 6, pp. 88-102.
Bronson et al., "Synthesis and Antiviral Activity of Phosphonylmethoxyethyl Derivatives of Purine and Pyrimidine Bases," in *Nucleotide Analogues as Antiviral Agents* (1989), ACS Symposium Series 401, American Chemical Society; Chapter 5, pp. 72-87.
Brown et al., "The Nucleophilic Displacement Route to Homochiral Arylphosphine Oxides," Tetrahedron, (1990) 46(13/14): 4877-4886.
Campagne et al. "Synthesis of Mixed Phosphonate Diester Analogues of Dipeptides using BOP or PyBOP Reagents," Tetra Lttrs., (1993) 34(42): 6743-6744.
Campbell D.A., "The Synthesis of Phosphonate Esthers; An Extension of the Mitsunobu Reation," J Org Chem. (1992) 57(23): 6331-6335.
Canas et al., "Regioselective Ring Opening of Chiral Epoxyalcohols by Primary Amines," Tetrahedron Ltts. (1991) 32(47): 6931-6934.
Casara et al., "Synthesis of Acid Stable 5'-o-Fluorometer Phosphonates of Nucleosides," Bioorg Med Chem Lett. (1992) 2(2): 145-148.
Casteel et al., "Steric and Electronic Effects in the Aryl Phosphate to Arylphoshonate Rearrangement," Synthesis, (1991) 1999(9): 691-693.
Chabner et al., "Purification and Properties of Cytidine Deaminase from Normal and Leukemia Granulocytes", J Clin Invest. (1974) 53: 922-931.
Chabner B.A., "Cytidine Analogues", in *Cancer Chemotherapy*,' Principles and Practice, Lippincott Williams & Wilkins (1990); Chapter 6; 154-179.
Chang et al., "Enhanced Cycophosphamide and Ifosfamide Activation in Primary Human Hepatocyte Cultures: Response to Cytochrome P-450 Inducers and Autoinduction by Oxazaphosphorines," Cancer Res. (1997) 57: 1946-1954.
Chen et al., "Intratumoral Activation and Enhanced Chemotheraputic Effect of Oxazaphosphorines following Cytochrome P-450 Gene Transfer: Development of a Combined chemptherapy/Cancer Gene Therapy Strategy," Cancer Res. (1995) 55: 581-589.
Chen et al. "Sensitization of Human Breast Cancer Cells to Cyclophosphamide and Ifosfamide by Transfer of al Liver Cytochrome P450 Gene," Cancer Res.(1996) 56: 1331-1340.
Chu et al., "A Regiospecific Synthesis of 1-Methylamino-6-fluoro-7-(4-methylpiperazin-1-yl)-1,4-dihydro-4-oxoguinoline-3-carboxylic Acid," J Het Chem. (1985) 22: 1033-1034.
Chu et al., "Chemistry and Antiviral Activities of Acyclonucleosides," J Het Chem. (1986) 23(2): 289-319.
Clarke et al., "Oxidative Metabolism of Cyclophosphamide: Identification of the Hepatic Monooxygenase Catalysts of Drug Activation," Cancer Res. (1989) 49: 2344-2350.
Coates et al., "Annelative Ring Expansion via Intramolecular [2+2] Photocycloaddition of $\alpha,\beta$-Unsaturated $\gamma$-Lactones and Reductive Cleavage: Synthesis of Hydrocyclopentacyclooctene-5-carboxylates," J Org Chem. (1982) 47(19): 4005.
Cohen, S.S. "The Mechanisms of Lethal Action of Arabinosyl Cytosine (araC) and Arabinosyl Adenine (araA)", Cancer (1977) 40(1): 509-518.
Commercon et al., "Diastereoselective Chlorocyclofunctionalization of N-Allylic Trichloroacetamides: Synthesis of an Analogue and Potential Precursor of RP49532," Tetrahed Ltts. (1990) 31(27): 3871-3874.
Cooper et al., "Use of Carbohydrate Derivatives for Studies of Phosphorus Stereo-chemistry. Part II. Synthesis and Configurational Assignments of 1,-3,2-Oxathiaphosphrinan-2-ones and 1,3,2-Dioxaphosphorinan-2-thiones," J.C.S. Perkin I, (1974) 3/2422:1049-1052.
Coppi, et al., "Lewis Acid Mediated Condensation of Alkenols and Aldehydes. A Selective Synthesis of Tetrahydropyrans and Oxepanes," J Org Chem., (1988) 53(4): 911-913.
Corey et al., "Enantioselective and Practical Syntheses of R- and S-Fluoxetines," Tetra Lttrs. (1989) 30(39): 5207-5210.
Cullis, P. M., "The Stereochemical Course of Iodine-Water Oxidation of Dinucleoside Phosphite Triesters," J Chem Soc. Chem. Commun., No. 1, 1984, pp. 1510-1512.
Cundy K.C., "Clinical pharmacokinetics of the antiviral nucleotide analogues cidofovir and adefovir," Clin Pharmacokinet. (1999) 36(2): 127-143.
Cundy et al., "Oral formulations of adefovir dipivoxil: in vitro dissolution and in vivo bioavailability in dogs," J Pharm Sci. (1997) 86(12): 1334-1338.
Curran et al., "Thermolysis of Bis[2-[(trimethylsilyl)oxy]prop-2-yl]furoXan (TOP—furoxan). The First Practical Method for Intermolecular Cycloaddition of an in Situ Generated Nitrile Oxide with 1,2-Di- and Trisubstituted Olefins," J Am Chem Soc. (1985) 107(21): 6023-6028.
Dang et al., "A New Regio-Defined Synthesis of PMEA," Nucleosides & Nucleotides (1998) 17(8): 1445-1451.
Davis et al., "Effect of *Withania somnifera* on cyclophosphamide-induced urotoxicity," Cancer Lett. (2000) 148: 9-17.
Dearfield et al., "Analysis of the Genotoxicity of Nine Acrylate/Methacrylate Coumpounds in L5178Y Mouse Lymphoma Cells," Mutagen. (1989) 4: 381-393 (1989).
Dechant et al., "Ifosfamide/Mesna—A Review of its Antineoplastic Activity, Pharmacokinetic Properties and Therapeutic Efficacy in Cancer," Drugs (1991) 42(3), 428-467.
De Clercq et al., "A novel selective broad-spectrum anti-DNA virus agent," Nature (1986) 323: 464-467.
De Clercq et al., "Antiviral activity of phosphonylmethoxyalkyl derivatives of purine and pyrimidines.," Antiviral Res. (1987) 8(5-6): 261-272.
Deeks et al., "The Safety and Efficacy of Adefovir Diplvoxil, a Novel Anti-Human Immunodeficiency Virus (HIV) Therapy, in HIV-Infected Adults: A, Randomized, Double-Blind, Placebo-Controlled Trial," J Infect Dis. (1997) 176(6): 1517-1523.
DeLeve et al., "Cellular Target of Cyclophosphamide Toxicity in the Murine Liver: Role of Glutathione and Site of Metabolic Activation," Hepatol. (1996) 24(4): 830-837.
De Lombaert et al., "N-Phosphomomethyl Dipeptides and Their Phosphonate Prodrugs, a New Generation of Neutral Endopeptidase (NEP, EC 3.4.24.11) Inhibitors", J Med Chem. (1994) 37(4): 498-511.

(56) References Cited

OTHER PUBLICATIONS

De Lombaert et al., "Pharmacological profile of a Non-Peptidic Dual Inhibitor of Neutral Endopeptidase 24.11 and Endothelin-converting enzyme," Biochem Biophys Res Commun. (1994) 204(1): 407-412.
Denmark et al., "Asymmetric Electrophilic Amination of Chiral Phosphorus-Stabilized Anions" Tetrahedron (1992) 48(11): 2191-2208.
Desos et al., "Structure-Activity Relationships in a Series of 2(1H)-Quinolones Bearing Different Acidic Function in the 3-Position: 6,7-Dichloro-2(1H)-oxoquinoline-3-phosphonic Acid, a New Potent and Selective AMPA/Kainate Antagonist with Neuroprotective Properties," J Med Chem. (1996) 39(1): 197-206.
Desta et al., "Stereoselective Metabolism of Cisapride and Enantiomer-Enantiomer Interaction in Human Cytochrome P450 Enzymes: Major Role of CYP3A,"J Pharmacol Exp Ther. (2001) 298(2): 508-520.
Dickson et al., "Orally Active Squalene Synthase Inhibitors: Bis((acyloxy)alkyl) Prodrugs of the alpha-Phosphonosulfonic Acid Moiety," J Med Chem. (1996) 39: 661-664.
Dornow et al., "Über einige Derivate der Benzoylessigsäure," in Chemische Berichte by C. Schöpf [Ed.], (1949) 82: 254-257.
Dyatkina et al., "Synthesis of the Four Possible Stereoisomeric 5'-Nor Carbocyclic Nucleosides from One Common Enantiomerically Pure Starting Material," Tetrahed Lttr. (1994) 35(13): 1961-1994.
Dymock, B.W., "Emerging Therapies for Hepatitis C Virus Infection," Expert Opin Emerg Drugs (2001) 6(1): 13-42.
Echizen et al., "Identifcation of CYP3A4 as the Enzyme Involved in the Mono-N-Dealkylation of Disopyramide Enantiomers in Humans," Drug Metab Dispos. (2000) 28(8): 937-944.
Edmunson et al., "Cyclic Organophosphorus Compounds, Part 23, Configurational Assignments in the 4-Phenyl-1.3,21ambd5-dioxaphosphorinane Series. X-Ray Molecular Structure of cis-2-Benzylamino-4-phenyl-1.3.2-dioxaphosphorinane 2-Oxide," J Chem Res Synop.(1989) 5: 122-123.
Eliel et al., "Oxygen-17 NMR Spectra of Cyclic Phosphites, Phosphates, and Tiophosphates", J Am Chem Soc. (1986) 108(21): 6651-6661.
Elliot et al., "Synthesis and Biological Evaluation of Phosphonamidate Peptide Inhibitors of Enkephalinas and Angiotensin-Converting Enxyme," J Med Chem. (1985) 28(9): 1208-1216.
Enriquez et al., "Conjugation of Aadenine Arabinoside 5'-Monophosphate to Arabinogalactan: Cynthesis, Characterization, and Antiviral Activity," Bioconj Chem. (1995) 6(2): 195-202.
Erion et al. "HepDirectTM Prodrugs for Targeting Nucleotide-Based Antiviral Drugs to the Liver" Curr Opin Invest Drugs (2006) 7(2): 109-117.
Erion et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver," J Am Chem Soc. (2004) 126(16): 5154-5163.
Erion et al., "Liver-Targeted Nucleoside Prodrugs," presented at the Gordon Research Conference: Purines, Pyrimidines and Related Substances, Newport, RI (Jun.-Jul. 2003), 38 pages.
Erion et al., "HepDirect(TM) Prodrugs: A Novel Strategy for Targeting Drugs to the Liver," Hepatology (2002) 36(4-2): Abstract No. 551, p. 301A.
Erion et al., "Prodrugs phosphorus-containing compounds and pharmacodynamic action", retrieved from STN Database accession No. 2001:808252; 1 pages.
Erion et al., "Preparation of cyclic nucleotides as FBPase inhibitor prodrugs" retrieved from STN Database accession No. 1999:576934; 4 pages.
Evans "Chemistry 206 Advanced Organic Chemistry", Harvard University, [online] Sep. 11, 2003, [retrieved on Jan. 19, 2005]. Retrieved from the internet, <http://www.courses.fas.harvard.edu/~chem206/Fall<SUB>-</SUB>2003/Lectures<SUB>-</SUB>and<SUB>-</SUB>Handouts/>.

Evans et al., "New Procedure for the Direct Generation of Titanium Enolates. Diastereoselective Bond Constructions with Representative Electrophiles," J Am Chem Soc. (1998) 112(22): 8215-8216.
Evans et al., "Stereoselective Aldol Reactions of Chlorotitanium Enolates. An Efficient Method of the Assemblage of Polypropionate-Related Synthons," J Am Chem Soc. (1991) 113(3): 1047-1049.
Fang, C., et al. "Liver-Targeting Prodrug of PMEA Induces a Much More Favorable Kidney and Liver Toxicological Gene Expression-in Rats Compared to BisPOM-PMEA" Abstract #1274, 42<SUP>nd </SUP>Annual Meeting of the Society of Toxicology, Salt Lake City, UT (Mar. 9-13, 2003).
Fang, C., et al., "Renal Toxicological Gene Response to Anti-Hepatitis B Prodrugs Hepavir B and Hepsera in Rats" Abstract #1472, 43<SUP>rd </SUP>Annual Meeting of the Society of Toxicology, Baltimore, MD (Mar. 21-25, 2004).
Farquhar et al., "Synthesis and Antitumor Evaluation of Bis[(pivaloyloxy)methyl] 2'-Deoxy-5-fluorouridine 5'-Monophosphate (FdUMP): A Strategy to Introduce Nucleotides into Cells," J Med Chem. (1994) 37(23): 3902-3909.
Farquhar et al. "Biologically-Cleavable Phosphate Protective Groups: 4-Aclioxt-1,3,2-Dioxaphosphorinanes as Neutral Latent Precursors of Dianionic Phosphates," Tetra Lttrs. (1995) 36(5): 655-658.
Farquhar et al., "5'-[4-(Pivaloyloxy)-1,3,2-dioxaphosphorinan 2 yl]2'-deoxy-5-fluorouridine: A membrane-permeating Prodrug of 5-fluoro-2'-deoxyuridylic acid (FdUMP)", J Med Chem. (1995) 38(3): 488-495.
Farquhar et al., "Biologically Reversible Phosphate-Protective Groups," J Pharm Sci. (1983) 72(3): 324-325.
Farquhar et al., "Synthesis and Biological Evaluation of Neutral Derivatives of 5-Fluoro-2'-deoxyuridine 5-Phosphate," J Med Chem. (1983) 26(8): 1153-1158.
Farquhar et al., "Synthesis and Biological Evaluation of 9-[5'-(2-Oxo-1,3,2-oxazaphosphorinan-2-y1)-beta-D-arabinosyl]adenine and 9-[5'-(Oxo-1,3,2-dioxazaphosphorinan-2-yl)-beta-D-arabinosyl]adenine: Potential Neutral Precursors of 9 [-62-D-Arabinofuranosyl]adenine 5'-Monophosphate,"J Med Chem. (1985) 28(9): 1358-1361.
Ferroni et al., "A Three-step Preparation of Dihydroxyacetone Phosphate Dimethyl Acetal", J Org Chem. (1999) 64(13): 4943-4945.
Fiume et al., "Inhibition of Hepatitis B Virus replication by Vidarbine Monophosphate Conjugated with Lactosaminated Serum Albumin," The Lancet (1988) 2: 13-15.
Fraiser et al., "Murine strain differences in metabolism and bladder toxicity of cyclophosphamide," Toxicol. (1992)75: 257-272.
Freed et al., "Evidence for Acyloxymethyyl Esters of Pyridmidenc, 5'-Deoxyribonucleotides as extracellular sources of active 5'-deoxyribonucleotides in cultured cells," Biochem Pharmcol. (1989) 38(19): 3193-3198.
Freeman et al., "Prodrug Design for Phosphates and Phosphonates", Chapter 3; Prog Med Chem. (1997) 34: 111-147.
Freer et al., "A new route to famiciclovir via palladium catalysed allylation", Tetrahedron (2000) 56(26): 4589-4595.
Friis et al., "Prodrugs of Phosphates and Phosphonates: Novel Lipophilic alpha-acyloxyalkyl Ester Derivatives of Phosphate—or Phosphonate Containing Drugs Masking the Negative Charges of these Groups," Euro J Pharm Sci., (1996) 4: 49-59.
Fujii et al.,"Ruthenium(II)-Catalyzed Asymmetric Transfer Hydrogenation of Ketones Using a Formic Acid-Triethylamine Mixture," J Am Chem Soc.(1996) 118: 2521-2522.
Furegati et al., "Stereochemistry of the Inhibition of alpha-Chymotrypsin with Optically Active cis-Decaline-Type Organosphosphates," <SUP>31</SUP>P-NMR Studies," Helvetica Chimica Acta (1998) 81: 1127-1138.
Gao et al., "Asymmetric Synthesis of Both Enantiomers of Tomoxetine and Fluoxetine. Seletive Reduction of 2,3-Epoxycinnamyl Alcohol with Red-A1," J Org Chem. (1988) 53(17): 4081-4084.
Gilard et al., "Chemical Stability and Fate of the Cytostatic Drug Ifosfamide and its N-Dechloroethylated Metabolites in Acidic Aqueous Solutions," J Med Chem. (1999) 42(14): 2542-2560.

(56) References Cited

OTHER PUBLICATIONS

Gilead Press Release, "Gilead Achieves Primary Endpoint in Phase III Study of Adefovir Dipivoxil for Chronic Hepatitis B Virus Infection," (2001); 3 pages.
Gish et al., "Nucleic Acids. 11. Synthesis of 5'-Esters of 1-beta-D-Arabinofuranosylcytosine Possessing Antileukemic and Immunosuppressive Activity", J Med Chem. (1971) 14(12): 1159-1162.
Gorenstein et al., "Stereoelectronic Effects in the Reactions of Epimeric 2-Aryloxy-2-oxy-1,3,2-dioxaphosphorinanes and Oxazaphosphorinanes," J Am Chem Soc. (1980) 102(15): 5077-5081.
Grant, S., "Biochemical Modulation of Cytosine Arabinoside", Pharmac Ther. (1990) 48: 29-44.
Greene et al., *Protective Groups in Organic Synthesis*, John Wiley, New York, 1999; (TOC only) 4 pages.
Groen et al., "Intracellular Compartmentation and Control of Alanine Metabolism in Rat Liver Parenchymal Cells," Eur J Biochem. (1982) 122: 87-93.
Guida et al., "Structure-Based Design of Inhibitors of Purine Nucleoside Phosphorylase. 4. A Study of Phosphate Mimics," J Med Chem. (1994) 37(8): 1109-1114.
Gurtoo et al., "Role of Glutathione in the Metabolism-dependent Toxicity and Chemotherapy of Cyclophosphamide," Cancer Res. (1981) 41: 3584-3591.
Gustin et al., "A Rapid, Sensitive Assay for Adenosine Deaminase," Anal Biochem. (1976) 71: 527-532.
Haddad et al., "Stereocontrolled Reductive Amination of 3-Hydroxy Ketones," Tetrahedron Ltts. (1997) 38(34): 5981-5984.
Hadváry et al., "Conformationally Restricted Analogs of Platelet-Activating Factor (PAF)", Helv Chim Acta 69(8): 1862-1871.
Hales et al., "Embryotoxicity of Phenyl Ketone Analogs of Cyclophosphamide," Teratology (1989) 39(1): 31-37.
Hanaoka et al., "Transformation of 2,3,9,10-tetraoxygenated protoberberine alkaloids into 2,3,10,11-tetraoxygenated protoberberine alkaloids", Heterocycles (1985) 23(11): 2927-2930.
Hanson et al., "Regioselective enzymatic aminoacylation of Lobucavir to give an intermediate for Lobucavir prodrug," Biorg Med Chem. (2000) 8(12): 2681-2687.
Harada et al., "Resolution of 1,3-alkanediols Via Chiral Spiroketals Derivatives from iota-Menthane," Tetra Lttr. (1987) 28(41): 4843-4846.
Harry-O'Kuru et al., "A short, flexible route toward 2'-C-branchedribonucleosides", J Org Chem. (1997) 62(6): 1754-1759.
Hatse S., "Mechanistic study on the cytostatic and tumor cell differentiation-inducing properties of 9-(2-phosphonylmethoxyethyl)adenine (PMEA, adefovir)-collected publications," Verh K Acad Geneeskd Belg. (2000) 62(5): 373-384.
Hayakawa et al., "A General Approach to Nucleoside 3'- and 5'-Monophospates", Tetra Lttrs. (1987) 28(20): 2259-2262.
Hayakawa et al., "Benzimidazolium Triflate as an Efficient Promoter for Nucleotide Synthesis via the Phosphoramidite Method," J Org Chem. (1996) 61(23): 7996-7997.
He et al., "Inactivation of Cytochrome P450 3A4 by Bergamottin, a Component of Grapefruit Juice," Chem Res Toxicol. (1998) 11(4): 252-259.
Hecker et al., "Prodrugs of Phosphates and Phosphonates", J Med Chem. (2008) 51(8): 2328-2345; publ online Feb. 1, 2008.
Hessler E.J., "An Efficient Synthesis of 1-beta-D-Arabinofuranosylcytosine," J Org Chem. 41(10):1828-1831 (1976).
Hillers et al., "Analogs of pyrimidinemono- and polynucleotides. VI. Phosphates of 1-(1,4-dihydroxy-2-pentyl) thymine and 1-(1,3-dihydroxy-2-propyl)uracil", Chemical Abstracts by The American Chemical Society (1978) 89 (17): 607-608; Chemical Abstr. 146864u.
Hilton J., "Role of Aldehyde Dehydrogenase in Cyclophosphamide-resistant L1210 Leukemia," Cancer Res. (1984) 44: 5156-5160.
Hirayama et al., "Structure and conformation of a novel inhibitor of angiotensin I converting enzyme-a tripeptide containing phosphonic acid," Int J Pept Protein Res. (1991) 38: 20-24.

Ho et al., "Cytotoxicity of cytotoxicity of antiviral nucleotides adefovir and cidofovir is induced by the expression of human renal organic anion transporter 1", J Am Soc Nephrol. (2000) 11(3): 383-393.
Hoeffler et al., "Chemical Synthesis of Enantiopure 2-C-Methyl-D-Erythritol 4-Phosphate, the Key Intermediate in the Mevalonate-Independent Pathway for Isoprenoid Biosynthesis", Tetrahed. (2000) 56(11): 1485-1489.
Hoffman M., "A Simple, Efficient Synthesis of Dibenzyl and Di-p-nitrobenzyl 1-Hydroxyalkanephosphonates," Synthesis, J Synth Org Chem. (1988) 1: 62-64.
Holy et al., "Acyclic nucleotide analogues: synthesis, antiviral activity and inhibitory effects on some cellular and virus-encoded enzymes in vitro," Antiviral Res. (1990) 13(6):295-311.
Hong Z., "Hepavir B: a Safer and Liver-Targeting Prodrug of PMEA," Presented at the SRI-Antiviral Drug Discovery & Development Summit, Ribopharm Inc., Mar. 27, 2003; 19 pages.
Hong et al., "Clinical Update of Remofovir (Hepavir B): a Liver-targeting Prodrug of PMEA for the Treatment of Hepatitis B," Presented at the SRI-Antiviral Drug Discovery & Development Summit, Mar. 30, 2004; 23 pages.
Hori et al., "Palladium(II)-Catalyzed Asymmetric 1,3-Dipolar Cycloaddition of Nitrones to 3-Alkenoyl-1,3-oxazolidin-2-ones," J Org Chem. (1999) 64(14): 5017-5023.
Hughes D.L., "The Mitsunobu Reaction," Org React. (1992) vol. 42, Chapt. 2, pp. 335-656.
Hulst et al.: "A New $^{31}$P NMR Method for the Enantiomeric Excess Determination of Alcohols, Amines and Amino Acid Esters," Tetra Lttrs. (1993) 34(8): 1339-1342.
Hunston et al., "Synthesis and Biological Properties of Some Cyclic Phosphotriesters Derived from 2'-Deoxy-5-fluorouride," J Med Chem. (1984) 27: 440-444.
Inanaga et al., "A Rapid Esterification by Means of Mixed Anhydride and its Application to Large-Ring Lactonization," Bull Chem Soc Jpn., (1979) 52(7): 1989-1993.
Iwata et al., "Asymmetric Functionalization at a Prochiral Carbon Center by the Aid of Sulfinyl Chirality: A Selective Formation of 6-Substituted (3R,Ss)—and (3S,Ss)-3-Hydroxymethyl-3,4-Dihydro-5-(p-Tolyl)Sulfinyl-2H-Pyrans," Tetra Lttrs. (1987) 28(27): 3131-3134.
Jacobsen et al., [Eds.] Comprehensive Asymmetric Catalysis—Catalysis I-III; Publisher: Springer (1999). (TOC only).
Jain et al., "Sulfonyl-Containing Aldophosphamide Analogues as Novel Anticancer Prodrugs Targeted against Cyclophosphamide-Resistant Tumor Cell Lines," J Med Chem. (2004) 47(15): 3843-3852.
Jones et al., "Minireview: nucleotide prodrugs", Antiviral Res. (1995) 27(1-2): 1-17.
Jones et al., "A Simple and Effective Method for Phosphoryl Transfer Using TiCl$_4$ Catalysis" Org. Lett. (2002) 4(21): 3671-3673.
Jounaidi et al., "Retroviral Transfer of Human Cytochrome P450 Genes for Oxazaphosphorine-based Cancer Gene Therapy," Cancer Res. (1998) 58(19): 4391-4401.
Jounaidi et al., "Frequent, Moderate-Dose Cyclophosphamide Administration Improves the Efficacy of Cytochrome P-450/Cytochrome P-450 Reductase-based Cancer Gene Therapy," Cancer Res. (2001) 61: 4437-4444.
Jung et al., "Hybridization of Alternating Cationic/Anionic Oligonucleotides to RNA Segments," Nucleosides and Nucleotides (1994) 13(6 & 7): 1597-1605.
Kachel et al., "Cyclophosphamide-Induced Lung Toxicity: Mechanism of Endothelial Cell Injury," J Pharmacol Exper Thera. (1994) 268(1): 42-46.
Keenan et al.,"Pathology Reevaluation of the Kociba et al. (1978) Bioassay of 2,3,7,8-TCDD: Implications for Risk Assessment," J Tox Envir Health (1991) 34: 279-296.
Kelley et al., "[[(Guaninylalkl) phosphinico]methyl]phosphonic Acids. Multisubstrate Analogue Inhibitors of Human Erythrocyte Purine Nucleoside Phosphorylase," J Med Chem. (1995) 38(6): 1005-1014.
Khamnei et al., "Neighboring Group Catalysis in the Design of Nucleotide Prodrugs," J Med Chem. (1996) 39(20): 4109-4115.

(56) References Cited

OTHER PUBLICATIONS

Khorana et al.,"Cyclic Phosphates. III. Some General Observations on the Formation and Properties of Five-, Six- and Seven-membered Cyclic Phosphate Esters," J Am Chem Soc. (1957) 79(2): 430-436.
Kim et al., "Synthesis and Biological Activities of Phosphonylalkylpurine Derivatives," Pharm. Res. Dev. (1989) 8(5-6): 927-931.
Kimura et al., "Studies on Nucleosides and Nucleotides. VII. 1) Preparation of Pyrimidine Nucleoside 5'-Phosphates and N3,5'-Purine Cyclonucleosides by Selective Activation of the 5'-Hydroxyl Group," Bull Chem Soc Jpn., (1979) 52(4): 1191-1196.
Kirschbaum, J., "Amantadine", Anal Prof Drug Subs. (1983) 12: 1-36.
Kirsten et al., "A General Strategy to Enantiomerically Pure Aliphatic and Olefinic Ketone Cyanohydrins by Stereoselective Alkylation of Umpoled Aldehyde Derivatives," J Org Chem. (1997) 62(20): 6882-6887.
Kobayashi et al., "Acylation of Active Methylene Compounds via Palladium Complex-Catalyzed Carbonylative Cross-Coupling of Organic Halides," Tetra Lttr., (1986) 27(39): 4745-4748.
Korba et al., "Liver-targeted Antiviral Nucleosides: Enhanced Antiviral Activity of Phosphatidyl-dideoxyguanosine in Woodchuck Hepatitis Virus Infection In Vivo," Hepatol. (1996) 25(5): 958-963.
Kramata et al., "9-(2-Phosphonylmethoxyethyl) derivatives of purine nucleotide analogs: A comparison of their metabolism and interaction with cellular DNA synthesis", Mol Pharmacol. (1999) 56(6): 1262-1270.
Krise et al., "Prodrugs of phosphates, phosphonates, and phosphinates," Adv Drug Del Rev. (1996) 19(2): 287-310.
Kryuchkov et al., "Influence of Solvent on the Strength of Cyclic Oxygen-Containing Phosphorus Acids," Bull Acad Sci USSR, A translation of Izvestiya Akademii Nauk SSSR, Ser. Khim. (1987) 36(6) Part 1: 1145-1148.
Kuriyama et al., "Transient Cyclophosphamide Treatment Before Intraportal Readministration of an Adenoviral Vector can Induce Re-expression of the Original Gene Construct in Rat Liver," Gene Thera. (1999) 6: 749-757.
Kwon et al., "Effects of N-Substitution on the Activation Mechanisms of 4-Hydroxycylophosphamide Analogues," J Med Chem. (1989) 32(7): 1491-1496.
Latour et al., "Simple Synthesis of 2-hydroxymethyl-1,3-propanediol and related compounds", Synthesis, 1987, 8: 742-745.
Lau et al., "Safety, Tolerability, Pharmacokinetics and Pharmacodynamics of Remofovir in Chronic HBV Patients in USA and Canada Following Daily Dosing for 28 Days," Presented at the 40th Annual Meeting of EASL, Paris, France, J Hepatology 42(Suppl. 2)132, Abstract No. 74, Elsevier Ireland Ltd. (Apr. 2005).
Leach et al. "Toxicity Studies in Mice Treated with 1-β-D-Arabinofuranosyl-cytosine (ara-C)", Cancer Res. (1969) 29: 529-535.
Lefebvre et al., "Mononucleoside Phosphotriester Derivatives with S-acyl-2-thioethyl Bioreversible Phosphate-protecting Groups: Intracellular Delivery of 3'azido-2',3'dideoxythymidine 5'-monophosphate," J Med Chem. (1995) 38(20): 3941-3950.
Li et al., "Enantiomer/Enantiomer Interactions between the S-and R- Isomers of Omeprazole in Human Cytochrome P450 Enzymes: Major Role of CYP2C19 and CYP3A44," J Pharmacol Exp Ther. (2005) 315(2): 777-787.
Li et al., "Synthesis of D-arabinofuranosides Using Propane-1,3-diyl Phosphate as the Anomeric Leaving Group," Tetrahed Ltts. (2001) 42: 6615-6618.
Lilo et al., Synthesis and Configurational Assignment of Bicyclic "Preactivated" Analogues of Cyclophosphamide, Tetra Lett. (1990) 31(6): 887-890.
Lin et al., "Comparative Disposition and Metabolic Profiles of [$^{14}$C]Remofovir and [$^{14}$C]Adefovir Dipivoxil in Rat Liver and Kidney," Abstracts of the 40th Annual Meeting of the European Association for the Study of the Liver, Paris, France, J Hepatology (2005) 42/2 Abstract #405;.

Lin et al., "Development of Hepavir B, A Prodrug of PMEA with Excellent Liver-Targeting Properties," Abstracts of the 39th Annual Meeting of the EASL, Berlin, Germany, J Hapatology (2004) 40: Abs No. 374; p. 112.
Lin et al. "Single-Dose Pharmacokinetics and Metabolism of [$^{14}$C]Remofovir in Rats and Cynomolgus Monkeys" Antimicrobial Agents Chemother. (2005) 49(3): 925-930.
Lin et al., "Pradefovir is a Substrate, but Neither an Inhibitor nor an Inducer for Cytochrome P450," AASALD Abstracts, Hepatology (2005) 514A: Abstract No. 811; 1 page.
Lin et al., "Remofovir Mesylate: a Prodrug of PMEA with Improved LIver-Targeting and Safety in Rats and Monkeys," Antiviral Chem Chemother. (2004) 15: 307-316.
Lin et al., "Safety, Tolerance, Pharmacokinetics and Pharmacodynamics of Remofovir, A Liver-Targeting Prodrug of PMEA in HBV Patients Following Daily Dosing for 28 Days," AASLD Abstracts No. 1141, Hepatology(2004) 40(4 Suppl.): 659A; 2 pages.
Löhr et al., "Targeted chemotherapy by intratumor injection of encapsulated cells engineered to produce CYP2B1, and ifosfamide activating cytochrome P450," Gene Thera. (1998) 5: 1070-1078.
Lok et al., "Neurotoxicity associated with adenine arabinoside monophosphate in the treatment of chronic hepatitis B virus infection," J Antimicrob Chemother. (1984) 14: 93-99.
Lorey et al., "A New Cyclic Phosphoramidate D4T Prodrug Approach *Cyclo*Amb-D4T-Phosphoramidates," Nucleo Nucleo. (1999) 18(4&5): 947-948.
Low et al., Conversion of 4-Hydroperoxycyclophosphamide and 4-Hydroxycyclophosphamide to Phosphoramide Mustard and Acrolein Mediated by Bifunctional Catalysts, Cancer Res. (1982) 42: 830-837.
Lown et al., "Grapefruit Juice Increases Felodipine Oral Availability in Humans by Decreasing Intestinal CYP3A Protein Expression," J Clin. Invest. (1997) 99: 2545-2553.
Lu et al., "Palladium-Catalyzed Reaction of Aryl Polyfluoroalkanesulfonates with O, O-Dialkyl Phosphonates", Synthesis (1987) 8: 726-727.
Ludeman et al., "Synthesis and Antitumor Activity of Cyclophosphamide Analogues. 1. Benzo Annulated Cyclophosphamide and Related Systems," J Med Chem. (1975) 18(12): 1251-1253.
Ludeman et al., "Synthesis and Antitumor Activity of Cyclophosphamide Analogues. 2. Preparation, Hydrolytic Studies, and Anticancer Screening of 5-Bromocyclophosphamide, 3,5-Dehydrocyclophosphamide, and Related Systems," J Med Chem. (1979) 22(2): 151-158.
Ludeman et al., Synthesis and Antitumor Activity of Cyclophosphamide Analogues. 4. Preparation, Kinetic Studies, and Anticancer Screening of "Phenylketophosphamide" and Similar Compounds Related to the Cyclophosphamide Metabolite Aldophosphamide, J Med Chem. (1986) 29(5): 716-727.
Ludeman et al., "Synthesis of Reactive Metabolite-Analogues of Cyclophosphamide for Comparisons of NMR Kinetic Parameters and Anticancer Screening Data," Drugs Exptl Clin Res. (1986) XII(6/7): 527-532.
Ma et al., "A Phase I/II Study to Assess the Safety, Tolerability and Pharmacokinetics (PK) of Intravenous (IV) Infusion of MB07133 in Subjects with Unresectable Hepatocellular Carcinoma (HCC) (Poster ID 2054, No. 19)", Poster Presentation; American Society of Clinical Oncology (ASCO) Conference, Atlanta, Georgia (Jun. 2006); 1 page.
MacKenna et al., "MB07133: A HepDirect(TM) Prodrug of Cytarabine Monophosphate for Use in Hepatocellular Carcinoma," Hepatol. (2003) 38(Suppl. 1):411A, AASALD Abstract No. 524, 1 page.
March, J. [Ed], "Effects of Structure on Reactivity" in *Advanced Organic Chemistry*, McGraw Hill Book Company, New York, (1977 2nd Ed.); Chapter 9, pp. 251-259.
Martin et al., "Synthesis and Antiviral Activity of Various Esters of 9-[1,3-Dihydroxyl-2-proposy)methyl]guanine," J Pharma Scie. (1987) 76(2): 180-184.

(56) References Cited

OTHER PUBLICATIONS

Matsushima et al., "The nucleotide and deduced amino acid sequences of porcine liver proline-β- naphthylamidase," FEBS. (1991) 293(1-2): 37-41.
May-Manke et al., "Investigation of the Major Human Hepatic Cytochrome P450 Involved in 4-Hydroxylation and N-dechlorethylation of Trofosfamide," Cancer Chemother Pharmacol. (1999) 44: 327-334.
Maynard-Faure et al., "New Strategy for the Diastereoselective Synthesis of Bicyclic 'Pre-activated' Analogues of Cyclophosphamide," Tetrahedron Lett. (1998) 39: 2315-2318.
McGuigan et al., "Intracellular Delivery of Bioactive AZT Nucleotides by Aryl Phosphate Derivatives of AZT," J Med Chem. (1993) 36(8): 1048-1052.
McGuigan et al., "Kinase Bypass: A new strategy for Anti-Hiv Drug Design," Bioorg Med Chem Lttrs. (1993) 3(6): 1207-1210.
Meek et al., "Synthesis of Inositol Phosphates", J Am Chem Soc. (1988) 110(7): 2317-2318.
Meier et al., "Cyclic Saligenyl Phosphotriesters of 2',3'-Dideoxy-2',3'-didehydrothymidine (d4T)—A New Pro-Nucleotide Approach," Bioorg Med Chem Lttrs. (1997) 7(2): 99-104.
Meier et al. "ADA-Bypass by Lipophilic cycloSal-ddAMP Pro-Nucleotides. A Second Example of the Efficiency of the cycloSal-Concept", Bioorg Med Chem Lett. (1997) 7(12): 1577-1582.
Meijer et al., "Covalent and Noncovalent Protein Binding of Drugs: Implications for Hepatic Clearance, Storage, and Cell-Specific Drug Delivery," Pharm Res. (1989) 6(2): 105-118.
Melvin, "An Efficient Synthesis of 2-Hydroxyphenylphosphonates," Tetra Lttrs. (1981) 22(35): 3375-3376.
Merckling et al., "Diastereoselectivity in Nucleophilic Displacement Reactions at Phosphorus; Isolation and Characterization of a Pentacoordinated Intermediate," Tetrahed Ltts. (1996) 37(13): 2217-2220.
Meyer et al., "2-O-Acyl-6-thioinosine Cyclic 3', 5'-Phosphates as Prodrugs of Thioinosinic Acid" , 3 Med Chem. (1979) 22(7): 811-815.
Mikolajczyk et al., "Dimethyl Selenoxide Oxidation of Trivalent Phosphorus Compounds, Thio- and Selenophosphoryl Compounds, and Thiocarbonyl Compounds. Stereochemical Studies and Selective Modification of the Thiocarbonyl-Containing Nucleic Acid Components," J Org Chem., (1978) 43(11): 2132-2138.
Misiura et al., "Synthesis and Antitumor Activity of Analogues of Ifosfamide Modified in the N-(2-Chloroethyl) Group," J Med Chem. (1987) 31(1): 226-230.
Mitchell et al., "Acetaminophen-Induced Hepatic Necrosis. IV. Protective Role of Glutathione," J Pharm Exp Thera. (1973) 187(1): 211-217.
Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J Chem Soc Perkin Trans. I. (1992) 2345-2353.
Mitsunobu, "The Use of Diethyl Azodicarboxylate and Triphenylphosphine in Synthesis and Transformation of Natural Products," Synthesis. (1981) 1981(1): 1-28.
Montag at al., "The Effect of Dexamethasone Treatment on CYP3A Activity Distribution, the Liver Targeting of MB07133 and CYP3A Activity in a Highly Proliferating State in Rats, " Hepatol. (2004) 40(Suppl. 1): 649A, AASALD Abstract No. 1123, 1 page.
Moore et al., "Comparison of Mutagenicity results for Nine Compounds evaluated at the hgprt Locus in the Standard and Suspension CHO Assays," Mutagenisis (1991) 6(1): 77-85.
Moriarty et al., "Diphenyl Methylphosphonate as a Phosphonylation Reagent with High Diastereoselectivity at Phosphorus," Tetrahedron Lett. (1997) 38(15): 2597-2600.
Mosbo et al. "Dipole Moment, Nuclear Magnetic Resonance, and Infrared Studies of Phosphorus Configurations and Equilibria in 2-R-2-Oxo-1,3,2-dioxaphosphorinanes," J Org Chem. (1977) 42(9): 1549-1555.
Mukaiyama, "The Directed Aldol Reaction", Org. React., (1982) 28: Chapter 3, pp. 203-251.
Mulato et al., "Nonsteroidal Anti-Inflammatory Drugs Efficiently Reduce the Transport and Cytotoxicity of Adefovir Mediated by the Human Renal Organic Anion Transporter 1," J Pharm Exp Ther. (2000) 295(1): 10-15.
Murono et al., "Prevention and inhibition of nasopharyngeal carcinoma growth by antiviral phosphonated nucleoside analogs," Cancer Res. (2001) 61(21): 7875-7877.
Murray et al., "Cytochrome P450 Expression is a common Molecular Event in Soft Tissue Sarcomas," J Phatol. (1993) 171: 49-52.
Murray et al., "Cytochrome P450 CYP3A in human renal cell cancer," Brit J Cancer (1999) 79(11/12): 1836-1842.
Naesens et al., "HPMPC (cidofovir), PMEA (adefovir) and Related Acyclic Nucleoside Phosphonate Analogues: A Review of Their Pharmacology and Clinical Potential in the Treatment of Viral Infections," Antiviral Chem Chemother., (1997) 8(1): 1-23.
Naesens et al., "Therapeutic Potential of HPMPC (Cidofovir), PMEA (Adefovir) and Related Acyclic Nucleoside Phosphonate Analogues as Broad-Spectrum Antiviral Agents," Nucleosides Nucleotides. (1997) 16(7-9): 983-992.
Nagamatsu et al., "New Phosphorylating Agents for General Synthesis of Mixed Phosphate Esters," Tetrahedron Lett. (1987) 28(21): 2375-2378.
Nakayama et al., "A Highly Enantioselective Synthesis of Phosphate Triesters," J Am Chem Soc. (1990) 112(19): 6936-6942.
Neidlein et al., "Mild Preparation of 1-Benzyloxyiminoalkylphosphonic Dichlorides: Application to the Synthesis of Cyclic Phosphonic Diesters and Cyclic Monoester Amides," Heterocycles (1993) 35(2): 1185-1203.
Nifant'Ev et al., et al., "Hexahydro-1,3,2,-Diazaphosphorines-II. Synthesis and Stereochemistry of Hexahydro-1,3-Dimethyl-1,3,4-Diazaphosphorines", J General Chemistry—USSR/Zh Obshch Khim., (1979) 49(1) Part 1: 53-61.
Nifantyev et al., "Synthesis and Structure of Some Stable Phospholane-Phospholanes," Phosphorus, Sulfur Silicon and Related Elements (1996) 113: 1-13.
Noble et al., "Adefovir Dipivoxil," Drugs. (1999) 58(3): 479-487.
Noyori et al., *Asymmetric Catalysis on Organic Synthesis*, (1994) John Wiley & Sons, Inc. (TOC only).
Ogg et al., "A reporter gene assay to assess the molecular mechanisms of xenobiotic-dependent induction of the human CYP3A4 gene in vitro," Xenobiotica (1999) 29(3): 269-279.
Ogilvie et al., A General Transesterification Method for the Synthesis of Mixed Trialkyl Phosphates, J Am Chem Soc. (1977) 99(1): 1277-1278.
Ohashi et al., "Synthesis of Phosphonosphingoglycolipid found in Marine Snail *Turbo Cornutus*," Tetra Lttrs. (1988) 29(10): 1189-1192.
Oliyai et al., "Kinetic Studies of the Degradation of Oxycarbonyloxymethyl Prodrugs of Adefovir and Tenofovir in Solution," Nucleosides, Nucleotides & Nucleic Acids, 20(4-7):1295-1298 (2001).
Ozaki et al, "Synthesis, Isolation and Characterization of Diastereochemically Pure Dithymidine Phosphormorpholidate Derivatives," Tetrahed Letts. (1989) 30(43): 5899-5902.
Ozaki et al., "Synthesis of Bis(deoxyribonucleoside) Phosphoromorpholidate Derivatives for Oligodeoxyribonucleotide Preparation by Use of a Selective Phosphitylating Reagent," Bull Chem Soc Jpn. (1989) 62(12): 3869-3876.
Ozoe et al., "Actions of cyclic esters, S-esters, and amides of phenyl-and phenylthiophosphonic acids on mammalia and insect GABA-gated chloride channels," Bioorg Med Chem. (1998) 6(1): 73-83.
Paine et al., "The Human Intestinal Cytochrome P450 'Pie'," Drug Metab Dispos. (2006) 34(5): 880-886.
Pankiewicz et al., "Nucleosides", J Org Chem. (1985) 50(18): 3319-3322.
Patois et al., "2-alkyl-5,5-dimethyl-1,3,2-dioxaphosphorinan-2-ones alpha-lithiated carbanions", J Chem Soc Perkin Trans. 1; (1990) 6: 1577-1581.
Patois et al., "Easy preparation of alkylphosphonyl dichlorides," Bull Soc Chim Fr. (1993) 130: 485-487.

(56) References Cited

OTHER PUBLICATIONS

Perich et al., "Di-*tert*-butyl N,N-Diethylphosphoramidite. A New Phosphitylating Agent for the Efficient Phosphorylation of Alcohols," Snthesis (1988) 1: 142-144.
Perich et al., "Synthesis of Casein-Related Peptides and Phosphopepties. V* The Efficient Global 'Phosphorylation of Protected Serine Derivatives and Peptides by Using Dibenzyl or Di-t-butyl N,N-Diethylphosphoramidite," Aust J Chem. (1990) 43(7-12): 1623-1632.
Perrillo et al., "A Multicenter United States—Canadian Trial to Assess Lamivudine Monotherapy before and after Liver Transplantation for Chronic Hepatitis B", Hepatol. (2001) 33(2): 424-432.
Petrakis et al., "Palladium-Catalyzed Substitutions of Triflates Derived from Tyrosine—Containing Peptides and Simpler Hydroxyarenes Forming 4-(Diethoxyphosphinyl) phenylalanines and Diethyl Arylphosphonates", J Am Chem Soc. (1986) 109(9): 2831-2833.
Pettit et al., "Antineoplastic agents 322. Synthesis of combretastatin A-4 prodrugs*," Anti-Cancer Drug Design. (1995) 10: 299-309.
Pilcher, "Built-In bypass," Nature (2004) 429: 39.
Plunkett et al. "Pharmacologically Directed Ara-C Therapy for Refractory Leukemia", Semin Oncol. (1985) 12(2) Supp. 3: 20-30.
Pogatchnik et al., "Enantioselective Synthesis of α-Hydroxy Phosphonates via Oxidation with (Camphorsulfonyl)oxaziridines," Tetrahedron Lett. (1997) 38(20): 3495-3498.
Posner et al., "3-Bromo-2-Pyrone: An Easily Prepared Chameleon Diene and a Synthetic Equivalent of 2-Pyrone in Thermal Diels-Alder Cucloadditions," Tetrahed Letts. (1991) 32(39): 5295-5298.
Postel et al., "Autocleavage of O-Isopropylidene Protected O-Phosphono- and O-Thionophosphono Esters of Sugars", J Carbohyd Chem. (2000) 19(2): 171-192.
Predvoditelev et al., "Glycero-2-hydroxymethylene phosphates" J Org Chem.—USSR (1977) 13(8) Part1: 1489-1492.
Predvoditelev et al., "Synthesis of lipids and their models on the basis of glycerol alkylene phosphites. V. Cyclic phosphatidylglycerol and phosphatidylhydroxyhomocholine" J Org Chem.—USSR (1981) 17(6) Part 2: 1156-1165.
Prisbe et al., "Synthesis and Antiherpes Virus Activity of Phosphate and Phosphonate Deriviates of 9-[(1,3-Dihydorzy-2-propoxy)methyl]guanine", J Med Chem (1986) 29: 671-675.
Quast et al., "Herstellung von Methylphosphonsäure-dichlorid," Synthesis, International Journal of Methods in Synthetic Organic Chemistry, 1974, p. 490.
Ramachandran et al., "Efficient General Synthesis of 1,2- and 1,3-diols in High Enantiomeric Excess via the Intramolecular Asymmetric Reduction of the Corresponding Ketoalkyl Diisopinocampheylborinate Intermediates," Tetra. Lttr. (1997) 38(5): 761-764.
Ramu et al., "Acrolein Mercapturates: Synthesis, Characterization, and Assessment of Their Role in the Bladder Toxicity of Cyclophosphamide," Chem Res TaxicoL. (1995) 8(4): 515-524.
Rao et al., "Studies Directed Towards the Synthesis of Immunosuppressive Agent FK-506: Synthesis of the Entire Top-Half," Tetrahedron Letts. (1991) 32(4): 547-550.
Rathore et al., "Synthesis of aryl dichlorophospates using phase transfer catalysts", Indian J Chem B. (1993) 32(10): 1066-1067.
Reddy et al., "Stereoselective Synthesis of Nucleoside Monophosphate HepDirect" Prodrugs, Tetra Lttrs. (2005) 46: 4321-4324.
Reddy et al., "Development of a Quantum Mechanics-Based Free-Energy Perturbation Method: Use in the Calculation of Relative Solvation Free Energies", J Am Chem Soc.(2004) 126(20): 6224-6225.
Reddy, K. Raja, et al., "Pradefovir (MB06866Q+): A Novel Hepatitis B Antiviral Therapy Using the HepDirect Prodrug Technology for Targeting Adefovir to the Liver," poster presented at the XVII International Roundtable on Nucleosides, Nucleotides and Nucleic Acids, Bern, Switzerland (Sep. 3-7, 2006).

Reddy, K. Raja, et al., "HepDirect™ Prodrugs of Adefovir: Design, Synthesis and Optimization," Abstract for 227th ACS National Meeting in Anaheim, CA (Mar. 28-Apr. 1, 2004).
Redmore, "Phosphorus Derivatives of Nitrogen Heterocycles. 2. Pyridinephosphonic Acid Derivatives," J Org Chem. (1970) 35(12): 4114-4117.
Ren et al., "Inhibition of Human Aldehyde Dehydrogenase 1 by the 4-Hydroxycyclophosphamide Degradation Product Acrolein," Drug Metabol Disp. (1999) 27(1): 133-137.
Ren et al. "Pharmacokinetlcs of cyclophosphamide and its metabolites in bone marrow transplantation patients," Clinical Pharm Thera. (1998) 64(3): 289-301.
Reusch, William, "Virtual Text of Organic Chemistry," Michigan State University, [online] Aug. 1, 2004, [retrieved on Jan. 19, 2005]. Retrieved from the internet, <http://www.cem.msu.edu/%7Ereusch/VirtualText/speciall2.htm#topl>.
Robins et al. "Design and synthesis of beta-D-ribofuranosyl nucleosides active against RNA viral infections", Adv Antiviral Drug Design. (1993) 1: 39-85.
Roodsari et al., "A new approach to the stereospecific synthesis of Phospholipids, etc.", J Org Chem. (1999) 64(21): 7727-7737.
Roy et al., "Development of a Substrate-Activity Based Approach to Identify the Major Human Liver P-450 Catalysts of Cyclophosphamide and Ifosfamide Activation Based on cDNA-Expressed Activities and Liver Microsomal P-450 Profiles," Drug Metab Dispos. (Mar. 1999) 27(6): 655-666.
Russell et al., "Determination of 9-[(2-phosphonylmethoxy)ethyl]adenine in rat urine by high-performance liquid chromatography with fluorescence detection," J Chromatogr. (1991) 572(1-2): 321-326.
Rustum et al. "1 β-Arabinofuranosylcytosine in Therapy of Leukemia: Preclinical and Clinincal Overview," Pharmac Ther. (1992) 56: 307-321.
Sakamoto et al., "The Palladium-Catalyzed Arylation of 4H-1,3-Dioxin,"Tetra Lttrs. (1992) 33(45): 6845-6848.
Sartillo-Piscil et al., "Fosfato-ésteres ciclicos diastereoisoméricos: 5-bromo-4-feni1-2-fenoxi-2-oxo-1,3,2-dioxafosforinanos,
precursores de radicales libres alquilo β-fosfatoxi y generadores de radicales cationicos en medio no oxidativo," Rev. Soc. Quim. Mexico 46(4): 330-334, Journal of the Mexican Chemical Society (Dec. 2002); English translation.
Schlachter et al., "Anti-Inflammatory/Antiarthritic Ketonic Bisphosphonic Acid Esters," Bioorg Med Chem. Lett. (1998) 8(9): 1093-1096.
Schultz, "Prodrugs of Biologically Active Phosphate Esters" Bioorg Med Chem. (2003) 11: 885-898.
Schultze et al., "Practical Synthesis of the anti-HIV Drug, PMPA" Tetrahedron Lett. (1998) 39(14): 1853-1856.
Schwartz et al., "Cyclophosphamide Induces Caspase 9-Dependent Apoptosis in 9L Tumor Cells," Mol Pharmacol. (2001) 60(6): 1268-1279.
Serafinowska et al., "Synthesis and in Vivo Evaluation of Prodrugs of 9-[2-(Phosphonomethoxy)ethoxy]adenine," J Med Chem. (1995) 38: 1372-1379.
Shan et al., "Prodrug Strategies Based on Intramolecular cyclization Reactions," J Pharm Sci. (1997). 86(7): 765-767.
Shaw et al., "Biological Screens of PMEA Prodrugs," Pharm Res. (1993) 10(10): S294, Contributed Papers Abstract No. PDD 7480.
Shaw et al., "Pharmacokinetics and Metabolism of Selected Prodrugs of PMEA in Rats," Drug Metabolism Dis. (1997) 25(3): 362-366.
Shen et al., "Nucleosides I. A New Synthesis of 1-β-D-Arabinofuranosyl Pyrimidine Nucleosides," J Org Chem. (1965) 30: 835-838.
Shih et al., "Preparation and Structures of 2-Dimethylamino-4-phenyl-1.3.2-dioxaphosphorinane-2-oxides," Bull Inst Chem Acad Sin. (1994) 41: 9-16.
Shih et al., "Synthesis and Structure of 6-Phenylcyclophosphamides," Heterocycles (1986) 24(6): 1599-1603.
Shih et al., "Studies on Potential Antitumor Agents (III). Synthesis of 4-Arylcyclophosphamides", Heterocycles (1978) 9(9): 1277-1285.

(56) References Cited

OTHER PUBLICATIONS

Shimada et al., "Interindividual Variations in Human Liver Cytochrome P-450 Enzymes Involved in the Oxidation of Drugs, Carcinogens and Toxic Chemicals: Studies with Liver Microsomes of 30 Japanes and 30 Caucasians," J Pharmacol Exp Ther. (1994) 270: 414-423.
Shimma et. al., "The Design and Sythesis of a New Tumor-Selective Fluoropyrimidine Carbamate, *Capecitabind*" Bioorg Med Chem. (2000) 8: 1697-1706.
Shirai et al., "Asymmetric Synthesis of Antimitotic CombretadioXolane with Potent Antitumor Activity Against Multi-Drug Resistant Cells," Bioorg Med Chem Lett (1998) 8: 1997-2000.
Silverberg et al., "A simple, rapid and efficient protocol for the selective phosphorylation of phenols with dibenzyl phosphite", Tetrahedron Lttrs. (1996) 37(6): 771-774.
Sladek et al. "Influence of Diuretics on Urinary General Base Catalytic Activity and Cyclophosphamide-Induced Bladder Toxicity", Canc Treat Repts. (1982) 65(11): 1889-1990.
Sladek et al., "Restoration of Sensitivity to Oxazaphosphorines by Inhibitors of Aldehyde Dehydrogenase Activity in Cultured Oxazaphosphorine-resistant L 1210 and Cross-Linking Agent-resistant P388 Cell Lines[1]," Canc Res. (1985) 45: 1549-1555.
Slowinski et al., "Highly Stereoselective Induction in the Cobald-mediated [2+2+2] Cycloaddition of Chiral Phosphine Oxides Substituted Linear Enediynes", Tetrahedron Ltts. (1999) 40: 5849-5852.
Smolarek et al., "Metabolism and cytotoxicity of acetaminopen in hepatocyte cultures from rat, rabbit, dog, and monkey", Drug Metab Dispos. (1989) 18(5): 659-663.
Springate et al. "Toxicity of Ifosfamide and It's Metaboline Chloroacetaldehyde in Cultured Renal Tubule Cells", In Vitro Cell Dev Biol.—Animal (1999) 35: 314-317.
Starrett et al., "Synthesis, Oral Bioavailability Determination, and in Vitro Evaluation of Prodrugs of the Antiviral Agent 9-[2-(Phosphonomethoxy)ethyl]adenine (PMEA)," J Med Chem. (1994) 37(12): 1857-1864.
Stepanov et al., "Total Syntheses of Chiral sn-myo-Inositol-1,4,5-Trisphosphate and its Enantiomer," Tetrahedron Letts. (1989) 30(38): 5125-5128.
Still et al "Direct Synthesis of Z-Unsaturated Esters. A Useful Modification of the Horner-Emmons Olefination," Tetrahedron LettS. (1983) 24(41): 4405-4408.
Stella V.J., "Prodrugs as Therapeutics", Expert Opin. Ther. Patents (2004) 14(3): 277-280.
Stowell et al., "The Mild Preparation of Synthetically Useful Phosphonic Dichlorides: Application to the Synthesis of Cyclic Phosphonic Diesters and Diamides," Tetrahedron Letts. (1990) 31(23): 3261-3262.
Strömberg et al, "Iodide and Iodine Catalysed Phosphorylation of Nucleosides by Phosphorodiester Derivatives," Nucleo Nucleo. (1987) 6(5): 815-820.
Sullivan-Bolyai et al., "Safety, Tolerability, Antiviral Activity, and Pharmacokinetics of Pradefovir Mesylate in Patients with Chronic Hepatitis B Virus Infection: 24-Week Interim Analysis of a Phase 2 Study," AASLD Program, Hepatol. (2005) 78A: Abstract No. LB 07.
Sumida et al., "Quantitative Analysis of Constitutive and Inducible CYPs mRNA Expression in the HepG2 Cell Line Using Reverse Transcription-Competitive PCR," Biochem Biophys Res Commun. (2000) 267(3): 756-780.
Suto et al. "The Effect of YNK-01 (an Oral Prodrug of Cytarabine) on Hepatocellular Carcinoma" Semin Oncol. (1997) 24(2) Suppl 6: S6-122 to S6-129.
Taapken et al., "Stereoselective Synthesis of Homochrial (E)-Vinyl Phosphonates Derived from (-)-Ephedrine," Tetrahedron Letts. (1995) 36(37): 6659-6662.
Takaku et al., "Synthesis of Bis(5-chloro-8-quinolyl) Nucleoside 5'-Phosphates in Oligoribonucleotide Synthesis by the Phosphotriester Approach," J Org Chem. (1982) 47(25): 4937-4940.

Takaku et al., "Synthesis of Deoxyribooligonucleotides Using Cesium Fluoride by the Phosphotriester Approach," Nippon Kagaku Kaisha (1985) 10: 1968-1973, The Chemical Society of Japan, Inc.; English Translation.
Takaku et al., "Use of 2-(2-Pyridyl)Ethyl Group as a new Protecting Group of Internucleotidic Phosphates in Oligonucleotide Synthesis", Chem Lttrs. (1986) 5: 699-702.
Tawfik et al., "1,8-Diazabicyclo[5.4.0]undecene Mediated Transesterification of p-Nitrophenyl Phosphonates: A Novel Route to Phosphono Esters," Synthesis (1993) 10: 968-972.
ten Hoeve et al.: "The Design of Resolving Agents Chiral Cyclic Phosphoric Acids," J Org Chem. (1985) 50(23): 4508-4514.
Thomson et al., "Synthesis, Bioactivation and Anti-HIV Activity of the Bis(4-acyloxybenzyl) and Mono(4-acyloxybenzyl) Esters of the 5'-monophosphate of AZT," J Chem Soc. Perkin Trans. I. (1993) 2/06723D: 1239-1245.
Thuong et al., "Nouvelle méthode de préparation de la phosphorylcholine, de la phosphorylhomocholine et de leurs dérivés," Bull Soc Chim France, (1974) No. 130; 1-2: 667-671; English translation.
Torneiro et al., "A Short, Efficient, Copper-Mediated Synthesis of 1alpha, 25-Dihydroxyvitamin D2 (1alpha, 25-Dihydroxyergocalciferol) and C-24 Analogs", J Org Chem. (1997) 62(18): 6344-6352.
Tullis et al., "Reagent Control of Geometric Selectivity and Enantiotopic Group Preference in Asymmetric Horner-Wadsworth-Emmons Reactions with meso-Dialdehydes," J Org Chem. (1998) 63(23): 8284-8294.
Turner et al., "Acylation of Ester Enolates by N-Methoxy-N-methylamides: An Effective Synthesis of beta-Keto Esters", J Org Chem. (1989) 54(17): 4229-4231.
Turner J. A., "A General Appproach to the Synthesis of 1,6-,1,7-, and 1,8-Naphthyridines," J Org Chem. (1990) 55(15): 4744-4750.
Valentine Jr., "Preparation of the Enantiomers of Compounds Containing Chiral Phosphorus Centers," Asym Synth. (1984) 41: 263-312.
Van Haperen et al., "Induction of Resistance to 2',2'-Difluorodeoxycytidine in the Human Ovarian Cancer Cell Line A2780", Semin Oncol. 22 Suppl. (1995) 11(4): 35-41.
Van Poelje et al., "MB6866 (Hepavir B), A HepDirect™ Prodrug of Adefovir: Mechanism of Activation and Liver Targeting," AASLD Abstracts, Hepatology (2003) 706A:Abstract No. 1143.
Vankayalapati et al., "Stereoselective synthesis of alpha-L-Fucp-(1,2)- and -(1,3)-beta-D-Galp(1)-4-methylumbelliferone using glycosyl donor substituted by propane-1,3-diyl phosphate as leaving group", 3 Chem Soc Perkin Trans J. (2000) 14: 2187-2193.
Venook, "Treatment of Heptacellular Carcinoma: Too Many Options?" J Clin Oncol. (1994) 12(6): 1323-1334.
Verfürth et al., "Asymmetrische Synthese chiraler Phosphorverbindungen durch destruktiv-selektive Oxidation von P(III)-Verbindungen mittels chiraler Oxaziridine," Chem. Ber. (1991) 124(7): 1627-1634.
Vitarella et al. "Hepavir B, A CYP3A4-Activated Prodrug of PMEA, Showed Better Safety then Hepsera in Pre-Clinical Studies" Abstract #995 of the 43rd Annual Meeting of the Society of Toxicology, Baltimore, MD (Mar. 2004).
Vo-Quang et al., "(1-Amino-2-propenyl) Phosphonic Acid, and Inhibitor of Alanine Racemase and D-Alanine:D-Alanine Ligase.," J Med Chem. (1986) 29(4): 579-581.
Wacher et al., "Active Secretion and Enterocytic Drug Metabolism Barriers to Drug Absorption," Adv Drug Del Rev. (2001) 46: 89-102.
Wada et al., "Nucleoside 3'-N,N-Dialkyphosphonamidates: Novel Building Blocks for Oligonucleotide Synthesis," Tetrahedron Letts. (1990) 31(44): 6363-6366.
Waga et al., "Synthesis of 4'-C-Methylnucleosides", Biosci Biotech Biochem. (1993) 57(9): 1433-1438.
Wagner et al., "Direct Conversion of Tetrahydropyranylated Alcohols to the Corresponding Bromides," Tetra Lttrs. (1989) 30(5): 557-558.
Wallace et al., "Design and Synthesis of Potent, Selective Inhibitors of Endothelin-Converting Enzyme," J Med Chem (1998) 41(9): 1513-1523.

(56) References Cited

OTHER PUBLICATIONS

Walsh et al. "Phenoxymethylphosphonic Acids and Phosphonic Acid Ion-exchange Resins," J Am Chem Soc. (1956) 78: 4455-4458.
Watanabe et al., "Dibenzyl Phosphorofluoridate, A New Phosphorylating Agent," Tetrahedron Letts. (1988) 29(45): 5763-5764.
Watanabe et al, "A Short Step and Practical Synthesis of MYO-Inositol 1,3,4,5-Tetrakisphosphate," Chem Pharm Bull. (1990) 38(2): 562-563.
Watkins et al., "Noninvasive tests of CYP3A enzymes," Pharmacogenetics (1994) 4: 171-184.
Weber et al., "Activation of the Anti-cancer Drug Ifosphamide by Rat Liver Microsomal P450 Enzymes," Biochem Pharm. (1993) 45(8): 1685-1694.
Wechter et al., "Nucleic Acids, 16. Orally Active Derivatives of ara-Cytidine", J Med Chem. (1976) 19(8), 1013-1017.
Weibel et al., "Potentiating Effect of {2-[2-[(2-Amino-1,6-Dihydro-6-oxo-9H-Purin-9-yl)Methyl]-Phenyl]Ethenyl}-Phosphonic Acid (MDL 74,428), A Potent Inhibitor of Purine Nucleoside Phosphorylase, on the Antiretroviral Activities of 2',3'-Dideoxyinosine Combined to Ribavirin in Mice, Biochem Pharmacol. (1994) 48(2): 245-252.
Weinhardt et al., "Synthesis and antidepressant Profiles of Phenyl-Substituted 2-Amino- and 2[(Alkoxycarbonyl)amino]-1,4,5,6-tetrahydropyrimidines[1]," J Med Chem. (1985) 28: 694-898.
Welch et al., "The Stereochemistry of the Aryl Phosphate/Aryl Phosphonate Rearrangement in 1,3,2-Oxazaphospholidine 2-Oxides," J Org Chem. (1990) 55(24): 5991-5995.
Werle et al., "Synthese der Dimethylolessigsäure," Liebigs. Ann. Chem., 1986, pp. 944-946.
Wileman et al., "Receptor-mediated endocytosis," Biochem J. (1985) 232: 1-14.
Wolfe et al., "A Concise Synthesis of 2'-C-Methylribonucleosides", Tetrahedron Lttrs. (1995) 36(42): 7611-7614.
Wolff M. E. [Ed] "Burger's Medicinal Chemistry and Drug Discovery, 5ed, Part I", John Wiley & Sons, 1995, pp. 975-977.
Woźniak et al., "Oxidation in Organophosphorus Chemistry: Potassium Peroxymonosulphate", Tetrahedron Letts. (1999) 40(13): 2637-2640.
Xu, C.R., et al. "Toxicokinetics of Adefovir Dipivoxil and Remofovir in 28-Day Toxicity Studies" Abstract #PB-P009 of the 64th International Congress FIP World Congress of Pharmacy and Pharmaceutical Science, New Orleans, LA (Sep. 2004).
Xu, C.R., et al., "Toxicokinetics of Remofovir in Mice, Rats and Monkeys After Repeated Oral Administrations" Abstract #PB-P008 of the 64th International Congress FIP World Congress of Pharmacy and Pharmaceutical Science, New Orleans, LA (Sep. 2004).
Yamakage et al., "1,1,1,3,3,3-Hexafluoro-2-Propyl Group as a New Phosphate Protection Group for Oligoribonucleotide Synthesis in the Phosphotriester Approach," Tetrahedron (1989) 45(17): 5459-5468.
Yamamoto et al., "Synthesis of Pyridine N-Oxide-SbC15 Complexes and Their Intramolecular and Oxygen-Transfer Reaction," Tetra Lttrs. (1981) 37: 1871-1873.
Yamanaka et al., "Metabolic Studies on BMS-200475, a New Antiviral Compound Active against Hepatitis B Virus", Antimicrob Agents Chemother. (1999) 43(1): 190-193.
Yip et al. "Use of High-Performance Liquid Chromatography in the Preparation of Flavin Adenine Dinucleotide Analyte Conjugates," J Chromatography (1985) 326: 301-310.
Yoshida et al., "Participation of the Peroxisomal β-Oxidation System in the Chain-Shortening of $PCA_{16}$, a Metabolite of the Cytosine Arabinoside Prodrug, YNKO1, in Rat Liver," Biochem Pharmacol. (1990) 39(10): 1505-1512.
Yu et al., "In Vivo Modulation of Alternative Pathways of P-450-Catalyzed Cyclophosphamide Metabolism: Impact on Pharmacokinetics and Antitumor Activity," J Pharm Exp Ther. (1999) 288(3): 928-937.
Yule et al., "The Effect of Fluconazole on Cyclophosphamide Metabolism in Children," Drug Metabo Disp. (1999) 27(3): 417-421.
Zon G., "Cyclophosphamide Analogues", *Progress Med Chem.*Ellis G.P. et al. [Eds] (1982) 19: 205-246.
Zon et al., "NMR Spectroscopic Studies of Intermediary Metabolites of Cyclophosphamide. A Comprehensive Kinetic Analysis of the Interconversion of cis- and trans-4-Hydroxycyclophosphamide with Aldophosphamide and Concomitant Partitioning of Adophosphamide Between Irreversible Fragmentation and Reversible Conjugation Pathways," J Med Chem. (1984) 27(4): 466-485.
Chen et al. "Conformation analysis of guanosine-5'-diphosphofucose". STN Database Accession No. 1996:144369. 1 page.
Chen et al. "Confirmation analysis of tunicamycin V and its natural substrate". STN Database Accession No. 1996: 204511. 3 pages.
Cote et al. "D-2 dopamine receptor-mediated inhibition of adenylate cyclase activity in the intermediate lobe of the rat pituitary gland requires guanosine 5' triphosphate". STN Database Accession No. 1982:159892; 2 pages.
Database Registry. Chemical Abstracts Service, Columbus, Ohio, US; Sep. 28, 2008. XP002777347, retrieved from STN Database Accession No. 1053732-62-9.
Database Registry. Chemical Abstracts Service, Columbus, Ohio, US; Sep. 28, 2008. XP002777348, retrieved from STN Database Accession No. 1053654-17-3.
Gududuru et al., "Identification of Darmstoff analogs as selective agonists and antagonists of lysophosphatidic acid receptors", Bioorg Med Chem Lett. (Dec. 31, 2006) 16:451-456.
Han et al., "Study of the prodrugs of peptide aldehydes as proteasome inhibitors", J Chin Pharma Sciences, (Dec. 31, 2012) 21:21-27.
Yang et al., "Effects of Guanosine Tetraphosphate, Guanosine Pentaphosphate, and β-γ Methylenyl-Guanosine Pentaphosphate on Gene Expression of *Escherichia coli*in Vitro" Proc. Nat. Acad. Sci. USA. vol. 71, No. 1, pp. 63-67, Jan. 1974.
Office Action dated Jan. 19, 2018, issued in related CN Application No. 201580008367.0.
Extended European Search Report dated Mar. 2, 2018, issued in corresponding EP Application No. 15815591.1.

* cited by examiner

PRODRUG COMPOUNDS AND USES THEROF

CROSS-REFERENCE TO RELATED APPLICATIONS

This application claims benefit of U.S. Provisional Application No. 62/020,044, filed on Jul. 2, 2014 and U.S. Provisional Application No. 62/152,341, filed on Apr. 24, 2015 both of which are incorporated herein by reference in their entirety.

FIELD

Compositions and methods in the field of medicine and chemistry are disclosed. Some of the disclosed embodiments are directed to medicinal dual and triple phosphorus containing prodrug compounds, medicinal compositions, as well as processes for their preparation and methods of their use. Some embodiments include prodrug compounds of acid/alcohol derivatives such as phosphates, phosphonates, phosphonamidates, phosphoramidates, carboxylates, phenolates, and alkoxyl, their preparation and their uses. In some embodiments, such prodrug compounds are useful to selectively deliver the acid/alcohol derivatives to the liver.

BACKGROUND

The following description of the background is provided to aid in understanding the invention, but is not admitted to be, or to describe, prior art to the invention.

Prodrugs are frequently used to improve certain properties of pharmacological agents for a preferred route of administration, including physicochemical, biopharmaceutical or pharmacokinetic properties. Certain prodrugs (also called soft drugs) are designed by tissue selective activation or deactivation to achieve therapeutic advantages (See J. Rautio, et al. Nature Reviews Drug Discovery 7: 255-270 (2008)).

Certain cyclic phosphate, phosphonate, phosphonamidate, and phosphoramidate prodrugs are disclosed in U.S. Pat. Nos. 6,312,662 and 7,205,404 and designed for liver-targeting of pharmacological agents. These prodrugs are activated by liver cytochrome P450 enzymes CYP3As that are predominantly expressed in the target tissue and designed to achieve the selective delivery of pharmacological agents to the liver. Since the prodrugs are not active outside the liver, the liver-targeting strategy reduces pharmacological or toxicological effects of a biologically active agent outside the targeting tissue. As a result, once used to treat liver diseases or to treat diseases via intervening in molecular pathways in the liver, the liver-targeting significantly improves patient benefit/risk ratio of a pharmacological agent (e.g. see M. D. Erion, et al. J Pharm Exp Ther 312:554-60 (2005)).

SUMMARY

Novel dual and triple phosphorus containing prodrug compounds of acid/alcohol derivatives such as phosphates, phosphonates, phosphonamidates, phosphoramidates, carboxylates, phenolates, and alkoxylates, their preparation and their uses are described. Some embodiments are related to novel prodrug compounds that do not generate a vinyl keto reactive intermediate in the activation process. Some embodiments are directed to the use of the prodrugs to enhance oral drug delivery. Some embodiments are directed to the use of the prodrugs to enhance efficiency to achieve higher triphosphate levels. Another aspect includes the use of prodrugs to treat diseases that benefit from enhanced drug distribution to the liver and like tissues and cells, including but not limited to hepatitis, cancer, liver fibrosis, fatty liver, malaria, other viral and parasitic infections, and metabolic, cardiovascular, and/or hormonal diseases where the liver is involved in the production and/or the homeostasis control of the biochemical end products, e.g. glucose, cholesterol, triglycerides, lipoproteins, apolipoproteins, and sex hormone-binding globulin (SHBG). Examples of such diseases include diabetes, hyperlipidemia, atherosclerosis, obesity and the like. In another aspect, prodrugs are used to prolong pharmacodynamic half-life of a drug. In some embodiments, the prodrug methodology can be used to achieve sustained delivery of the parent drug. In another aspect, prodrugs are used to increase the therapeutic index of the drug. In some embodiments, the prodrugs are useful in the delivery of diagnostic imaging agents to the liver. Some additional embodiments relate to a method of making prodrugs.

Some embodiments of the compounds, compositions, and methods provided herein include a compound of Formula I:

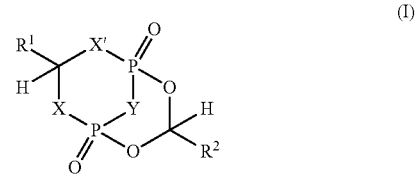

(I)

wherein:
$R^1$ and $R^2$ are independently selected from the group consisting of H, M, an optionally substituted $C_1$-$C_6$ alkyl, an optionally substituted $C_1$-$C_6$ hereroalkyl, an optionally substituted $C_2$-$C_6$ alkenyl, an optionally substituted aryl, and an optionally substituted heteroaryl;
M is a biological agent or part of a biological agent or a prodrug of a biological agent;
X and X' are independently O or $NR^3$;
Y is selected from the group consisting of a bond, O, S, $NR^4$, $Si(R^4)_2$, and an optionally substituted $C_1$-$C_6$ alkyl;
$R^3$ is selected from the group consisting of H, a $C_1$-$C_6$ alkyl, and a $C_1$-$C_6$ heteroalkyl;
$R^4$ is selected from the group consisting of H, an optionally substituted $C_1$-$C_6$ alkyl, an optionally substituted $C_1$-$C_6$ heteroalkyl, an optionally substituted aryl, and an optionally substituted heteroaryl;
or a stereoisomer or a pharmaceutically acceptable salt thereof.

Some embodiments of the compounds, compositions, and methods provided herein include a compound of Formula II:

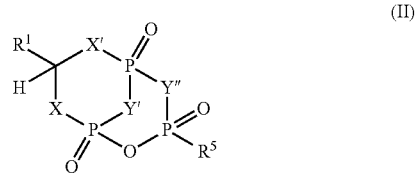

(II)

wherein:
$R^1$ is selected from the group consisting of H, M, an optionally substituted $C_1$-$C_6$ alkyl, an optionally substituted $C_1$-$C_6$ hereroalkyl, an optionally substituted $C_2$-$C_6$ alkenyl, an optionally substituted aryl, and an optionally substituted heteroaryl;

$R^5$ is selected from the group consisting of M, Cl, OH, $NH_2$, an optionally substituted $C_1$-$C_6$ alkyl, an optionally substituted $C_1$-$C_6$ alkyloxy, and an optionally substituted alkylamino;

M is a biological agent or part of a biological agent or a prodrug of a biological agent;

X and X' are independently O or $NR^3$;

Y' and Y" are independently selected from the group consisting of O, S, an optionally substituted $CH_2$, and $NR^3$;

$R^3$ is selected from the group consisting of H, a $C_1$-$C_6$ alkyl, and a $C_1$-$C_6$ heteroalkyl;

or a stereoisomer or a pharmaceutically acceptable salt thereof.

Some embodiments of the compounds, compositions, and methods provided herein include a compound of Formula III:

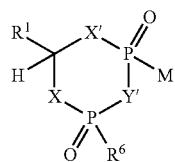

(III)

wherein:

$R^1$ is selected from the group consisting of H, M, an optionally substituted $C_1$-$C_6$ alkyl, an optionally substituted $C_1$-$C_6$ hereroalkyl, an optionally substituted $C_2$-$C_6$ alkenyl, an optionally substituted aryl, and an optionally substituted heteroaryl;

$R^6$ is selected from the group consisting of Cl, OH, $NH_2$, an optionally substituted $C_1$-$C_6$ alkyl, an optionally substituted $C_1$-$C_6$ alkyloxy, an optionally substituted alkylamino, and —$OP(O)(R^7)_2$;

$R^7$ is selected from the group consisting of OH, an optionally substituted $C_1$-$C_6$ alkyl, and an optionally substituted $C_1$-$C_6$ alkyloxy;

M is a biological agent or part of a biological agent or a prodrug of a biological agent;

X and X' are independently O or $NR^3$;

Y' is selected from the group consisting of O, S, an optionally substituted $CH_2$, and $NW^3$;

$R^3$ is selected from the group consisting of H, a $C_1$-$C_6$ alkyl, and a $C_1$-$C_6$ heteroalkyl;

or a stereoisomer or a pharmaceutically acceptable salt thereof.

Some embodiments of the compounds, compositions, and methods provided herein include a compound of Formula IV:

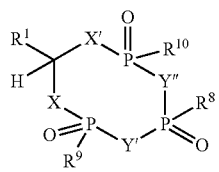

(IV)

wherein:

$R^1$ is selected from the group consisting of H, M, an optionally substituted $C_1$-$C_6$ alkyl, an optionally substituted $C_1$-$C_6$ hereroalkyl, an optionally substituted $C_2$-$C_6$ alkenyl, an optionally substituted aryl, and an optionally substituted heteroaryl;

$R^8$ and $R^9$ are independently selected from the group consisting of M, Cl, OH, $NH_2$, an optionally substituted $C_1$-$C_6$ alkyl, an optionally substituted $C_1$-$C_6$ alkyloxy, and an optionally substituted alkylamino;

$R^{10}$ is selected from the group consisting of Cl, OH, NH2, an optionally substituted $C_1$-$C_6$ alkyl, an optionally substituted $C_1$-$C_6$ alkyloxy, and an optionally substituted alkylamino;

M is a biological agent or part of a biological agent or a prodrug of a biological agent;

X and X' are independently O or $NR^3$;

$R^3$ is selected from the group consisting of H, a $C_1$-$C_6$ alkyl, and a $C_1$-$C_6$ heteroalkyl;

Y' and Y" are independently selected from the group consisting of O, S, an optionally substituted $CH_2$, and $NR^3$;

or a stereoisomer or a pharmaceutically acceptable salt thereof.

In some embodiments, M is a nucleoside antiviral or anticancer agent.

In some embodiments, M is a lipid modulator.

In some embodiments, M is a nuclear hormone receptor modulator.

Some embodiments of the compounds, compositions, and methods provided herein include a pharmaceutical composition comprising any of the compounds provided herein and a pharmaceutically acceptable excipient.

Some embodiments of the compounds, compositions, and methods provided herein include a method of treating a disease or condition in the liver in a subject comprising administering an effective amount of any of the compounds provided herein to a subject in need thereof.

Some embodiments of the compounds, compositions, and methods provided herein include a method of treating a disease or condition by intervening in a molecular pathway/target (e.g. a receptor or an enzyme or the like) in the liver in a subject comprising administering an effective amount of any of the compounds provided herein to a subject in need thereof.

Some embodiments also include administering an effective amount of additional therapeutic agent to the subject in need thereof.

In some embodiments, the subject is a mammal.

In some embodiments, the subject is a human.

Some embodiments of the compounds, compositions, and methods provided herein include the use of any one of the compounds provided herein for treating a disease in the liver or a disease or condition in which the physiological or pathogenic pathways involve the liver in a subject.

Some embodiments also include the use of any one of the compounds provided herein in combination with an additional therapeutic agent.

Some embodiments of the compounds, compositions, and methods provided herein include any one of the compositions provided herein for use in the preparation of a medicament for treating a disease or condition in the liver or a disease or condition in which the physiological or pathogenic pathways involve the liver.

DETAILED DESCRIPTION

The present embodiments are directed to compositions and methods related to novel cyclic dual and triple phosphorus containing prodrug compounds of biologically active acid/alcohol derivatives such as phosphates, phosphonates, phosphonamidates, phosphoramidates, carboxylates, phenolates, and alkoxylates, their preparation and their uses.

Example activation of some cyclic phosph(on)ate and phosphoramidate compounds are illustrated below:

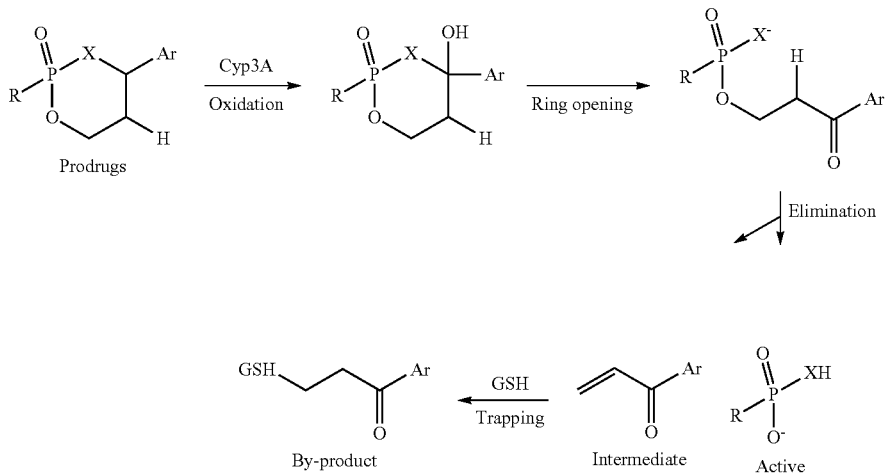

In the above example, the cyclic prodrugs (X=O or N) are oxidized by Cyp3A in the liver and undergo a ring opening and β-elimination sequence to provide the active drugs and an aryl vinyl ketone (Intermediate). The latter is rapidly conjugated with glutathione (GSH) that exists in millimole levels in the liver to yield the conjugate by-product.

Certain oral available pharmaceutical agents have been described to have certain liver-targeted property (e.g. see X. J. Zhou, et al. 2009 EASL, meeting poster #966). The liver-targeting effects of these agents are based on liver first-pass metabolism of an orally administered agent and the liver-targeting efficiency varies widely, depending upon the pharmacokinetic property of the agent, and are not as efficient as the Cyp3A activated prodrugs.

Nucleoside based pharmacological agents are given as a prodrug form either as a nucleoside or its derivative, or monophosphate or its derivative. The prodrug is activated in the cell to form biologically active nucleoside triphosphates by nucleoside kinases. The first phosphorylation of nucleoside to form nucleoside monophosphate is often a slower process and, as a result, the monophosphate based prodrugs are typically superior than the prodrug of non-phosphorylated nucleoside drugs.

Bisphosphonate cyclic acetal compounds have been used as prodrug for more efficient oral delivery of bisphosphonate drugs in treatment of osteoporosis and other calcium and phosphate related disorders (e.g., see US 2011/0098251).

Some examples of novel cyclic dual and triple phosphorus containing prodrug compounds and their stereoisomers and pharmaceutically acceptable salts are represented by Formula I, II, III, and IV:

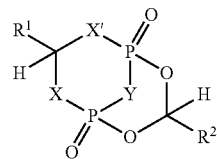 (I)

-continued

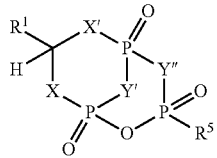 (II)

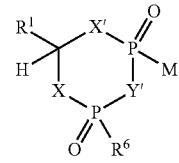 (III)

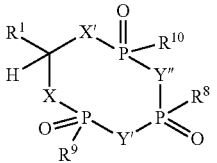 (IV)

wherein:
$R^1$ and $R^2$ are independently selected from the group consisting of H, M, an optionally substituted $C_1$-$C_6$ alkyl, an optionally substituted $C_1$-$C_6$ hereroalkyl, an optionally substituted $C_7$-$C_6$ alkenyl, an optionally substituted aryl, and an optionally substituted heteroaryl;

$R^3$ is selected from the group consisting of H, a $C_1$-$C_6$ alkyl, and a $C_1$-$C_6$ heteroalkyl;

$R^4$ is selected from the group consisting of H, an optionally substituted $C_1$-$C_6$ alkyl, an optionally substituted $C_1$-$C_6$ heteroalkyl, an optionally substituted aryl, and an optionally substituted heteroaryl;

$R^5$ is selected from the group consisting of M, Cl, OH, $NH_2$, an optionally substituted $C_1$-$C_6$ alkyl, an optionally substituted $C_1$-$C_6$ alkyloxy, and an optionally substituted alkylamino;

$R^6$ is selected from the group consisting of Cl, OH, $NH_2$, an optionally substituted $C_1$-$C_6$ alkyl, an optionally substituted $C_1$-$C_6$ alkyloxy, an optionally substituted alkylamino, and —OP(O)($R^7$)$_2$;

$R^7$ is selected from the group consisting of OH, an optionally substituted $C_1$-$C_6$ alkyl, and an optionally substituted $C_1$-$C_6$ alkyloxy;

$R^8$ and $R^9$ are independently selected from the group consisting of M, Cl, OH, $NH_2$, an optionally substituted $C_1$-$C_6$ alkyl, an optionally substituted $C_1$-$C_6$ alkyloxy, and an optionally substituted alkylamino;

$R^{10}$ is selected from the group consisting of Cl, OH, $NH_2$, an optionally substituted. $C_1$-$C_6$ alkyl, an optionally substituted $C_1$-$C_6$ alkyloxy, and an optionally substituted alkylamino;

M is a biological agent or part of a biological agent or a prodrug of a biological agent;

X and X' are independently O or $NR^3$;

Y is selected from the group consisting of a bond, O, S, $NR^4$, $Si(R^4)_2$, and an optionally substituted $C_1$-$C_6$ alkyl;

Y' and Y" are independently selected from the group consisting of O, S, an optionally substituted $CH_2$, and $NR^3$;

or a stereoisomer or a pharmaceutically acceptable salt thereof.

In some embodiments, the cyclic dual or triple phosphorus containing prodrug compounds of Formula I, II, III, and IV are substrates of cytochrome p450 isozymes CYP3As, a family of monooxygenase enzymes. Known prodrugs of a different class (e.g. see M. D. Erion, et al. J Pharm Exp Ther 312:554-60 (2005)) are oxidized by CYP3A4 as the first activation step, but then generate an α,β-unsaturated carbonyl intermediate compound by a β-elimination reaction to complete the activation. Since certain α,β-unsaturated carbonyl compounds are toxic and/or have mutagenic activity, prodrugs activated by CYP3As without involvement of the β-elimination offer advantages in overall drug safety. In some embodiments, the novel prodrug compounds of Formula I, II, III, and IV do not generate a vinyl keto reactive intermediate in the activation process.

CYP3A4 is expressed in the liver at a level much higher than other tissues (DeWaziers et al. J Pharm Exp Ther 253:387 (1990)). Prodrug compounds of Formula I, II, III, and IV are predominantly activated via CYP3A4 in the liver. In some embodiments, the cyclic phosphorus prodrug compounds of Formula I, II, III, and IV have high efficiency in liver-targeting via selective delivery of biologically active agents to the liver. In some embodiments, the prodrugs are used to increase the therapeutic index of the drug, since the prodrug compounds of Formula I, II III, and IV may not be active or may be less active outside the liver.

In some embodiments, the cyclic dual or triple phosphorus containing prodrug compounds of Formula II, III, and IV where M is a nucleoside or a nucleoside derivative are activated in the liver to directly generate a nucleoside diphosphate or triphosphate. In some embodiments, the cyclic phosphorus prodrug compounds of Formula II, III, and IV have higher efficiency in liver-targeting than that of nucleoside monophosphate prodrug compounds via selective delivery of higher orders of phosphates to the liver.

In some embodiments, the cyclic triple phosphorus containing prodrug compounds of Formula III and IV where M is a nucleoside or a nucleoside derivative are activated in the liver to directly generate a nucleoside diphosphate. In some embodiments, the cyclic phosphorus prodrug compounds of Formula III and IV have higher efficiency in liver-targeting than that of nucleoside monophosphate prodrug compounds via selective delivery of biologically active triphosphates to the liver.

In some embodiments, the cyclic triple phosphorus containing prodrug compounds of Formula II where M is a nucleoside or a nucleoside derivative are activated in the liver to directly generate a novel nucleoside cyclic triphosphate. In some embodiments, the novel cyclic triphosphates generated in the liver from prodrug compounds of Formula II may have unique biological and/or pharmacokinetic activities.

In some embodiments, the prodrug compounds of Formula I, II, III, and IV are used to treat diseases that benefit from enhanced drug distribution to the liver and like tissues and cells, including but not limited to diseases in the liver, such as hepatitis, liver cancer, liver fibrosis, fatty liver, malaria, other viral and parasitic infections, and metabolic, cardiovascular, and/or hormonal diseases where the liver is involved in the production and/or the homeostasis control of biochemical end products, e.g. glucose (e.g. diabetes); cholesterol, fatty acids, bile acids, triglycerides (e.g. hyperlipidemia, atherosclerosis and obesity), lipoproteins, apolipoproteins, and sex hormone-binding globulin (SHBG).

In some embodiments, the disclosed prodrugs are used to prolong pharmacodynamic half-life of the drug. In addition, the disclosed prodrug methodology can be used to achieve sustained delivery of the parent drug. In some embodiments, a method of making these prodrugs is described. In some embodiments, the prodrugs are also useful in the delivery of diagnostic imaging agents to the liver or other tissues.

Certain compounds of Formula I, II, III, and IV have asymmetric centers where the stereochemistry is unspecified, and the diastereomeric mixtures of these compounds are included, as well as the individual stereoisomers when referring to a compound of Formula I, II, III, and IV generally.

Some embodiments of the compounds, compositions and methods provided herein include a pharmaceutical composition comprising a compound provided herein and a pharmaceutically acceptable carrier.

Some embodiments also include administering an effective amount of a second or multiple therapeutic agents in combination with a compound provided herein to the subject in need thereof.

Some embodiments of the compounds, compositions and methods provided herein include a method of treating liver diseases such as hepatitis and liver cancer, comprising administering an effective amount of a compound provided herein where M is an antiviral or anticancer nucleoside such as a HCV polymerase inhibitor, a reverse transcriptase inhibitor, a DNA synthesis inhibitor, a RNA synthesis inhibitor, and/or an antimetabolic agent to a subject in need thereof.

Some embodiments of the compounds, compositions and methods provided herein include a method of treating dyslipidemia and fatty liver comprising administering an effective amount of a compound provided herein where M is a lipid modulator such as a HMG-CoA reductase inhibitor, a selective thyroid hormone receptor modulator, a peroxisome proliferator-activated receptor modulator, a fibrate, a DGAT inhibitor, a nicotinic acid, a bile acid, a folic acid and a fatty acid to a subject in need thereof.

Some embodiments of the compounds, compositions and methods provided herein include a method of treating hyperglycemia comprising administering an effective amount of a compound provided herein where M is a glucose modulator such as peroxisome proliferator-activated receptor modulator, glucose biosynthesis inhibitor, and/or dipeptidyl peptidase 4 inhibitor to a subject in need thereof.

Some embodiments of the compounds, compositions and methods provided herein include a method of treating a hormonal condition comprising administering an effective amount of a compound provided herein where M is a nuclear hormone receptor modulator to a subject in need thereof.

In some embodiments, the subject is mammalian.

In some embodiments, the subject is human,

Some embodiments of the compounds, compositions and methods provided herein include a method of testing a compound in a cell comprising contacting the cell with the disclosed compounds.

Some embodiments of the compounds, compositions and methods provided herein include use of a compound provided herein in the treatment of a disease in the liver.

Some embodiments include the use of a compound provided herein in combination with additional therapeutic agent(s) for the treatment of a disease in the liver.

Some embodiments of the compounds, compositions and methods provided herein include use of a compound provided herein in the treatment of a disease or condition by intervening in a molecular pathway in the liver.

Some embodiments include the use of a compound provided herein in combination with additional therapeutic agent(s) for the treatment of a disease or condition by intervening in a molecular pathway in the liver.

Definitions

In accordance with the present disclosure and as used herein, the following terms are defined with the following meanings, unless explicitly stated otherwise. It is to be understood that both the foregoing general description and the following detailed description are examples and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting.

As used herein, ranges and amounts can be expressed as "about" a particular value or range. "About" also includes the exact amount. Hence "about 10%" means "about 10%" and also "10%."

As used herein, "optional" or "optionally" means that the subsequently described event or circumstance does or does not occur, and that the description includes instances where the event or circumstance occurs and instances where it does not. For example, an optionally substituted group means that the group is unsubstituted or is substituted.

As used herein, the singular forms "a," "an" and "the" include plural referents unless the context clearly dictates otherwise. Thus, for example, reference to a composition comprising "a therapeutic agent" includes compositions with one or a plurality of therapeutic agents.

The term "alkyl" refers to saturated aliphatic groups including straight-chain, branched chain and cyclic groups, up to and including 10 carbon atoms. Suitable alkyl groups include methyl, ethyl, n-propyl, isopropyl, and cyclopropyl. The alkyl group may be optionally substituted with 1-3 substituents.

The term "optionally substituted" or "substituted" includes groups substituted by one to four substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, carboxamido, nitro, lower acyloxy, lower aminoalkyl, lower alkylaminoaryl, lower alkylaryl, lower acylaminoalkyl, lower alkoxyaryl, lower arylamino, lower aralkylamino, lower alkylsulfonyl, lower carboxamidoalkylaryl, lower carboxamidoaryl, lower hydroxyalkyl, lower haloalkyl, lower alkylaminoalkylcarboxy, lower aminocarboxamidoalkyl, cyano, lower alkoxyalkyl, lower perhaloalkyl, and lower arylalkyloxyalkyl. "Substituted aryl" and "substituted heteroaryl" refers to aryl and heteroaryl groups substituted with 1-6 substituents. These substituents are selected from the group consisting of lower alkyl, lower alkoxy, lower perhaloalkyl, halogen, hydroxy, cyano, and amino.

The term "heteroalkyl" refer to alkyl groups containing at least one heteroatom, such as 1 to 3 heteroatoms. Suitable heteroatoms include oxygen, sulfur, and nitrogen.

The term "heteroacyl" refer to —C(O)-heteroalkyl groups.

The term "acyloxy" refers to —OC(O)R where R is alkyl, or heteroalkyl.

The term "alkoxy" or "alkyloxy" refers to OR where R is alkyl, or heteroalkyl, all optionally substituted.

The term "carboxyl" refers to a C(O)OH.

The term "oxo" refers to an =O group.

The term "oxo derivative" refers to =NR where R is H, lower alkyl, lower alkoxyl, or lower alkylamino.

The term "amino" refers to NRR' where R and R' are each independently selected from hydrogen, alkyl, aryl, aralkyl and heterocycloalkyl, all except H are optionally substituted; and R and R' can form a cyclic ring system.

The term "halogen" or "halo" refers to F, Cl, Br and I.

The term "haloalkyl" refer to alkyl groups containing at least one halogen, in a further aspect are 1 to 3 haloatoms. Suitable haloatoms include F, Cl, and Br.

The term "haloheteroalkyl" refer to alkyl groups containing at least one halogen and one heteroatom.

The term "haloacyl" refer to —C(O)-haloalkyl groups.

The term "haloheteroacyl" refer to —C(O)-haloheteroalkyl groups.

The term "alkenyl" refers to unsaturated groups which have 2 to 12 atoms and contain at least one carbon carbon double bond and includes straight chain, branched chain and cyclic groups. Alkenyl groups may be optionally substituted. Suitable alkenyl groups include allyl.

The term "alkenyl'" refers to unsaturated groups which have 2 to 12 atoms and contain at least one carbon carbon triple bond and includes straight chain, branched chain and cyclic groups. Alkynyl groups may be optionally substituted. Suitable alkenyl groups include ethynyl.

The term "methylene" refers to =CH$_2$.

The term "methylene derivative" refers to =CRR' where R and R' are each independently selected from an optionally substituted alkyl and an optionally substituted alkenyl.

The term "aminoalkyl" refers to the group NR$_2$-alkyl where R is selected from H, alkyl, aryl, aralkyl, and heterocycloalkyl.

The terms "alkylamino" refers to the group alkyl-NH— or (alkyl)$_2$-N—.

The term "amido" refers to the NR$_2$ group next to an acyl or sulfonyl group as in NR$_2$C(O)—, RC(O)NR$_2$—, NR$_2$S(=O)$_2$— and RS(=O)$_2$—NR$_2$—, where R includes H, alkyl, aryl, aralkyl, and heterocycloalkyl.

The term "perhalo" refers to groups wherein every C—H bond has been replaced with a C-halo bond on an aliphatic or aryl group. Suitable perhaloalkyl groups include $CF_3$ and $CFCl_2$.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted. Examples of aryl groups include, but are not limited to phenyl, naphthalenyl, phenanthrenyl, anthracenyl, tetralinyl, fluorenyl, indenyl, and indanyl.

The term "heteroaryl" refers to an aromatic group wherein at least one atom forming the aromatic ring is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $G_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In some embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$alkyl, hydroxy-$C_{1-6}$-alkyl, and amino-$C_{1-6}$-alkyl.

The phrase "therapeutically effective amount" means an amount of a compound or a combination of compounds that partially or fully ameliorates, attenuates or eliminates one or more of the symptoms of a particular disease or condition or prevents, modifies, or delays the onset of one or more of the symptoms of a particular disease or condition. Such amount can be administered as a single dosage or can be administered according to a regimen, whereby it is effective. Repeated administration may be needed to achieve a desired result (e.g., treatment of the disease and/or condition).

The term "pharmaceutically acceptable salt" includes salts of compounds of Formula I, III and IV and their prodrugs derived from the combination of a compound of the present embodiments and an organic or inorganic acid or base. Suitable acids include acetic acid, adipic acid, benzenesulfonic acid, (+)-7,7dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis-[3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid.

Where the number of any given substituent is not specified (e.g., "haloalkyl"), there may be one or more substituents present. For example, "haloalkyl" can include one or more of the same or different halogens. For example, "haloalkyl" includes each of the substituents $CF_3$, $CHF_2$ and $CH_2F$.

The term "patient" refers to an animal being treated including a mammal, such as a dog, a cat, a cow, a horse, a sheep, and a human. In some embodiments the patient is a mammal, either male or female. In some embodiments, the patient is a male or female human, The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, HOOPR$_2$—, associated with the drug, that cleave in vivo. Standard prodrugs include hut are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are examples, not exhaustive, and one skilled in the art could prepare other known varieties of prodrugs. Prodrugs must undergo some form of a chemical transformation to produce the compound that is biologically active or is a precursor of the biologically active compound in some cases, the prodrug is biologically active, usually less than the drug itself, and serves to improve drug efficacy or safety through unproved oral bioavailability, pharmacodynamic half-life, etc. Prodrug forms of compounds may he utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site specific delivery of the compound.

The term "stereoisomer" refers to the relative or absolute spatial relationship of the R group(s) attached to the stereogenic centers either carbon or phosphorus atoms, and refers to individual or any combination of the individual isomers such as a racemic mixture and a diastereomeric mixture. When a compound has two stereogenic centers, there are 4 potential stereoisomers. When a compound has three stereogenic centers, there are 8 potential stereoisomers.

The term "liver" refers to the liver organ.

The term "liver specificity" refers to the ratio:

[drug or a drug metabolite in liver tissue]/[drug or a drug metabolite in blood or another tissue]

as measured in animals treated with the drug or a prodrug. The ratio can be determined by measuring tissue levels at a specific time or may represent an AUC (area under a curve) based on values measured at three or more time points, The term "increased or enhanced liver specificity" refers to an increase in liver specificity ratio in animals treated with the prodrug relative to animals treated with the parent drug. Compounds disclosed in U.S. Pat. No. 8,063,025, U.S. Pat. No, 7,666.855, and PCT Pub. No. WO2009/073506, are designed for the liver-specific delivery of nucleosides for the treatment of HCV patients and take advantage of a cytochrome P450 enzyme that is mainly expressed in the liver.

The term "enhanced oral bioavailability" refers to an increase of at least about 50% of the absorption of the dose of the parent drug. In an additional aspect, the increase in oral bioavailability of the prodrug (compared to the parent drug, is at least about 100%, or a doubling of the absorption. Measurement of oral bioavailability usually refers to measurements of the prodrug, drug, or drug metabolite in blood, plasma, tissues, or urine following oral administration compared to measurements following parenteral administration.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The terms "treating" or "treatment" of a disease includes inhibiting the disease (slowing or arresting or partially arresting its development), preventing the disease, providing relief from the symptoms or side effects of the disease (including palliative treatment), and/or relieving the disease (causing regression of the disease).

The terms "biological agent" refers to a compound that has biological activity or that has molecular properties that can be used for therapeutic or diagnosis purposes, such as a compound carrying a radioactive isotope or a heavy atom.

The terms "molecular pathway" refers to a series of molecular events in tissues such as a receptor modulating sequence, an enzyme modulating sequence, or a biosynthesis sequence that is involved in physiological or pathophysiological functions of a living animal.

Formulations

The disclosed compounds may be used alone or in combination with other treatments. These compounds, when used in combination with other agents, may be administered as a daily dose or an appropriate fraction of the daily dose (e.g., bid). The compounds may be administered after a course of treatment by another agent, during a course of therapy with another agent, administered as part of a therapeutic regimen, or may be administered prior to therapy by another agent in a treatment program.

Examples of pharmaceutically acceptable salts include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Compositions containing the active ingredient may be in any form suitable for the intended method of administration. In some embodiments, the compounds of a method and/or composition described herein can be provided via oral administration, rectal administration, transmucosal administration, intestinal administration, enteral administration, topical administration, transdermal administration, intrathecal administration, intraventricular administration, intraperitoneal administration, intranasal administration, intraocular administration and/or parenteral administration.

When the compounds are administered via oral administration, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient can be mixed with an inert solid diluent, for example calcium phosphate or kaolin, or as soft gelatin capsules wherein the active ingredient can be mixed with water or an oil medium, such as peanut oil, liquid paraffin or olive oil.

Formulations suitable for parenteral administration include aqueous and non-aqueous isotonic sterile injection solutions which may contain, for example, antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

In some embodiments unit dosage formulations contain a daily dose or unit, daily sub-dose, or an appropriate fraction thereof, of a drug. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Synthesis of Compounds

The following procedures for the preparation of the cyclic prodrug compounds illustrate the general procedures used to prepare the prodrug compounds. Prodrugs can be introduced at different stages of synthesis of a drug. In some embodiments, they are made at a later stage, because of the general sensitivity of these groups to various reaction conditions. Optically pure prodrugs containing a single isomer at the phosphorus center can be made, for example, by separation of the diastereomers by a combination of column chromatography and/or crystallization, or by enantioselective synthesis of chiral activated phosph(on)ate intermediates.

Scheme I describes general strategies of synthesis of the bicyclic prodrug compounds of Formula I. Diphosphate compound 1 is condensed with an aldehyde of structure 2 in the presence of catalytic amount of acid to give a product of structure 3. The aldehyde compound of structure 2 is prepared from the corresponding carboxylic acid. Second condensation of compounds of structure 3 with the second aldehyde affords the final bicyclic compounds of structure 5. Alternative approaches take advantages of aldehyde equivalent compounds such as compounds 6 and 7 to provide products 3 and 5 under basic conditions.

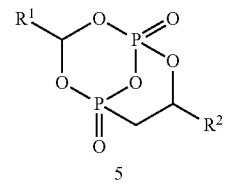

Scheme II describes general strategies of synthesis of the bicyclic prodrug compounds of Formula H. Treatment of the bisphosphonate of structure 6 with phosphorus oxychloride yields cyclic phosphate chloride of structure 7 that is reacted with an alcohol derivative to introduce an $R^5$ group to form the compound of structure 8. A condensation reaction between the compound of structure 8 and an aldehyde under acidic conditions provides a final bicyclic compound of structure 9. Alternatively, the bisphosphonate of structure 6 is condensed with an aldehyde to form a compound of structure 10 that is then treated with phosphorus oxychloride to give an intermediate of structure 11. Displacement of the chloride in a compound of structure 11 with an alcohol affords the final compound of structure 9.

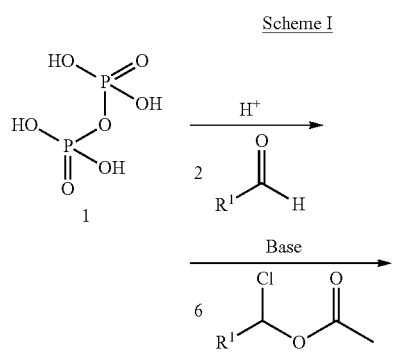

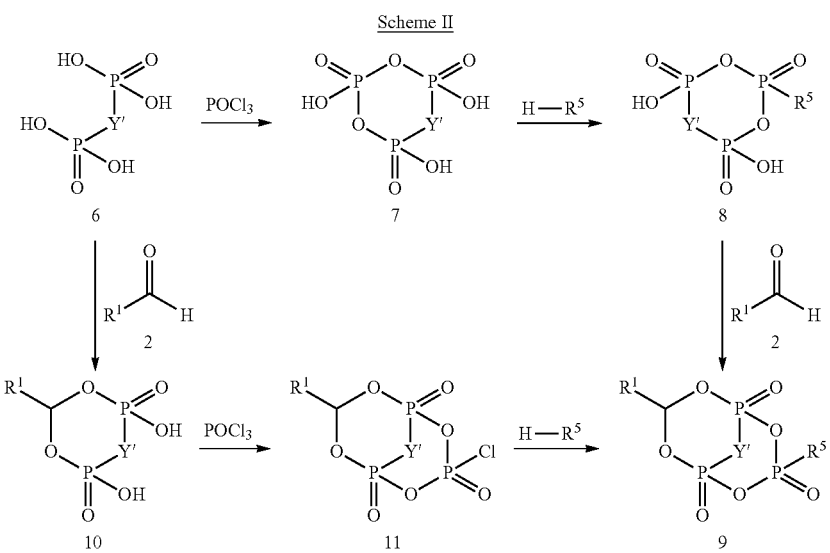

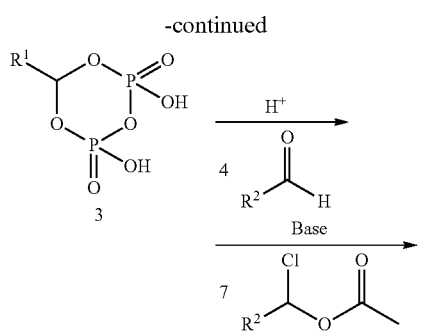

Scheme III describes general strategies of syntheses of the cyclic prodrug compounds of Formula III. Condensation of the bisphosphonic chloride of structure 12 and an aldehyde of structure 2 generates the intermediate of structure 13 that is then treated with an alcohol of H—M and an alcohol of H—$R^6$ to yield final product of structure 14. Alternatively, phosphonic acid of structure 15 is treated with a phosphorus oxychloride derivative to provide an intermediate of structure 16 that is condensed with an aldehyde of structure 2 to afford the final product.

Scheme III

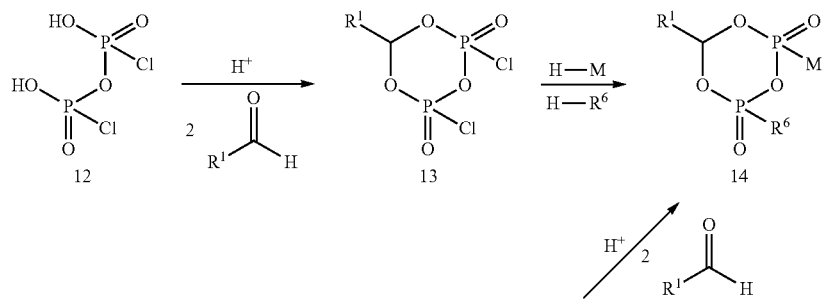

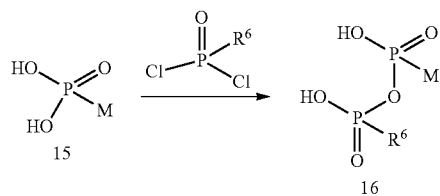

Scheme IV describes general strategies of synthesis of the cyclic prodrug compounds of Formula. IV. A phosphonic acid chloride of structure 16 is prepared from phosphorus oxychloride and an alcohol and then phosphorylated to give the triphosphate derivative of structure 17 with pyrophosphate. Cyclization of the triphosphate derivative of structure 17 with an aldehyde of structure 2 provides the final product of structure 18. Alternatively, the cyclic intermediate of structure 20 is formed from the triphosphate derivative of structure 19 and an aldehyde and then is activated to the intermediate of structure 21. Treatment of the phosphorus chloride of structure 21 with an alcohol provides the final product of structure 18.

Scheme IV

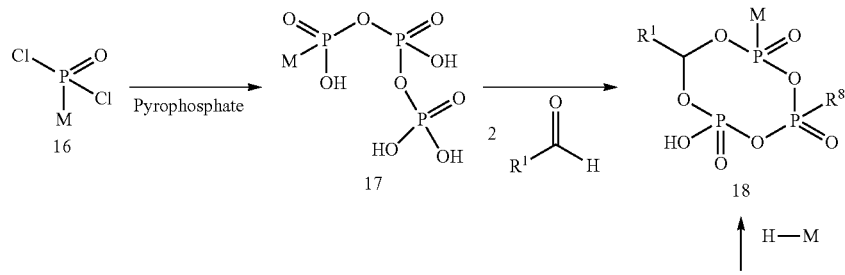

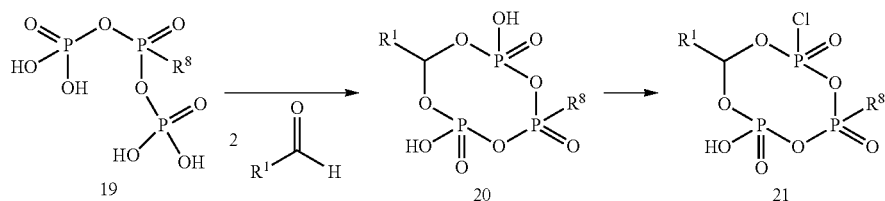

EXAMPLES

It will be understood that the following are examples and that the present embodiments are not limited to these examples. The sample compounds are prepared to demonstrate the synthetic methodologies as outlined below without attaching a biologically active agent.

Example 1

2,4-Dihydroxy-6-phenethyl-1,5,2,4-dioxadiphosphinane 2,4-dioxide (Compound 101)

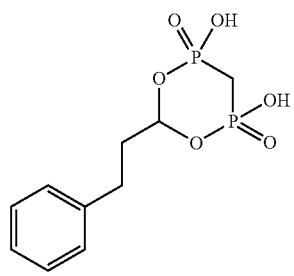 [SMILES: O=P1(O)CP(=O)(O)OC(CCc2ccccc2)O1]

Compound 101 was prepared according to the general procedure of Scheme I as a triethylamine salt from 3-phenylpropanal and methylenebis(phosphonate). Treatment of 3-phenylpropanal (1.34 g, 10 mmol) with excess neat zinc triflate at 0° C. In the presence of acetyl chloride (1.2 g, 15 mmol) for 2 hours provided 1-chloro-3-phenylpropyl acetate (1.7 g, 80% yield). The resulting acetate (128 mg, 0.6 mmol) was then treated with methylenebis(phosphonate) (53 mg, 0.3 mmol) in acetonitrile in the presence of DIPEA (392 mg, 3.0 mmol) at 45° C. overnight. The mixture was worked up by standard procedure and prep-HPLC with $Et_3NHCO_3$ as buffer provided Compound 101 as a triethylamine salt. $[M+H]^+$ calcd for $C_{10}H_{14}O_6P_2$: 293.03; found: 293.05. $^1$H NMR (300 MHz, $CD_3OD$) 7.28-7.06 (m, 5H), 5.67-5.57 (m, 1H), 3.17 (q, J=7.4, 6H), 2.76 (t, J=8.1, 2H), 2.38 (t, J=28, 2H), 2.07-1.92 (m, 2H), and 1.29 (t, J=7.4, 9H). $^{31}$P NMR (300 MHz, $CD_3OD$) 14.883 (s).

Example 2

2,4-Dihydroxy-6-phenethyl-1,3,5,2,4-trioxadiphosphinane 2,4-dioxide (Compound 102)

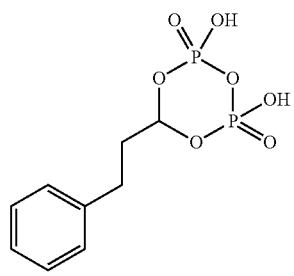 [SMILES: O=P1(O)OC(CCc2ccccc2)OP(=O)(O)O1]

Compound 102 was prepared as a triethylamine salt from 3-phenylpropanal and pyrophosphate in the same fashion as described in Example 1. $[M+H]^+$ calcd for $C_9H_{12}O_7P_2$: 295.01; found: 2.95.15. $^1$H NMR (300 MHz, $CD_3OD$) 7.30-7.12 (m, 5H), 5.33 (t, J=4.5, 1H ), 3.19 (q, J=7.4, 6H), 2.75 (t, J=7.5, 2H), 2.08-1.95 (m, 2H), and 1.30 (t, J=7.4, 9H).

Example 3

2,4-Dihydroxy-6-phenyl-1,3,5,2,4-trioxadiphosphinane 2,4-dioxide (Compound 103) and 3,7-diphenyl-2,4,6,8,9-pentaoxa-1,5-diphosphabicyclo[3.1.1]nonane 1,5-dioxide (Compound 104)

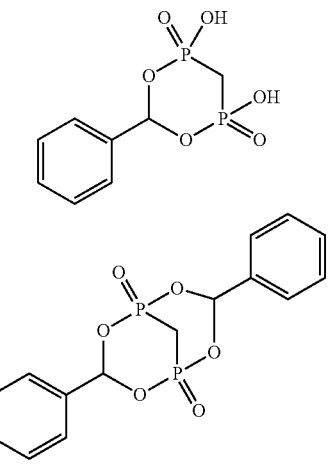

Compounds 103 and 104 were prepared from benzaldehyde and methylenebis(phosphonate) in a same fashion as described in Example 1. Compound 103 was isolated as DIPEA double salt, $[M-H]^-$ calcd for $C_8H_{10}O_6P_2$: 263.00; found: 263.00. $^1$H NMR (300 MHz, $CD_3OD$) 7.62-7.58 (m, 2H), 7.41-7.30 (m, 3H), 6.65 (bs, 1H), 3.78-3.61 (m, 4H), 3.22-3.06 (m, 4H), 2.40-2.02 (m, 2H), and 1.40-1.20 (m, 30H). $^{31}$P NMR (300 MHz, $CD_3OD$) 14.345 (s). Compound 104, $[M+H]^+$ calcd for $C_{15}H_{14}O_6P_2$: 353.03; found: 353.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A compound of Formula III:

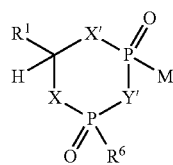

wherein:
- $R^1$ is selected from the group consisting of, M, an optionally substituted $C_1$-$C_6$ alkyl, an optionally substituted $C_1$-$C_6$ heteroalkyl, an optionally substituted $C_2$-$C_6$ alkenyl, an optionally substituted aryl, and an optionally substituted heteroaryl;
- $R^6$ is selected from the group consisting of Cl, OH, $NH_2$, an optionally substituted $C_1$-$C_6$ alkyl, an optionally substituted $C_1$-$C_6$ alkyloxy, an optionally substituted alkylamino, and —OP(O)(R)$_2$;
- $R^7$ is selected from the group consisting of OH, an optionally substituted $C_1$-$C_6$ alkyl, and an optionally substituted $C_1$-$C_6$ alkyloxy;
- M is a biological agent or part of a biological agent or a prodrug of a biological agent;
- X and X' are independently O or $NR^3$
- Y' is O;
- $R^3$ is selected from the group consisting of H, a $C_1$-$C_6$ alkyl, and a heteroalkyl;

or a stereoisomer or a pharmaceutically acceptable salt thereof.

2. The compound of claim 1, wherein M is a nucleoside antiviral or anticancer agent.

3. The compound of claim 1, wherein M is a lipid modulator.

4. The compound of claim 1, wherein M is a nuclear hormone receptor modulator.

5. The compound claim 1, wherein M is at least one selected from the group consisting of: a HCV polymerase inhibitor, a reverse transcriptase inhibitor, a DNA synthesis inhibitor, an RNA synthesis inhibitor, and an antimetabolic agent.

6. A pharmaceutical composition comprising the compound of claim 1 and a pharmaceutically acceptable excipient.

7. A method of treating a disease, disorder or condition in the liver of a subject comprising:
administering an effective amount of the compound of claim 1 to a subject in need thereof.

8. A method of treating a disease, disorder or condition by intervening in a molecular pathway or target in the liver in a subject comprising:
administering an effective amount of the compound of claim 1 to a subject in need thereof.

9. A method of treating a disease, disorder or condition in the liver or a disease, disorder or condition in which the physiological or pathogenic pathways involve the liver in a subject, comprising:
administering an effective amount of the compound of claim 1 to the subject.

10. A method of treating hepatitis, liver cancer, liver fibrosis, malaria, viral infection, parasitic infection, cancer, fatty liver, diabetes, hyperlipidemia, atherosclerosis, obesity, dyslipidemia, hyperglycemia or a hormonal condition in a subject comprising:
administering an effective amount of the compound of claim 1 to the subject.

11. The method of claim 7, further comprising administering an effective amount of an additional therapeutic agent to the subject in need thereof.

12. The method of claim 7, wherein the subject is a mammal.

13. The method of claim 7, wherein the subject is a human.

14. A method of intervening in a molecular pathway or modulating a target in a cell comprising contacting the cell with the compound of claim 1.

15. The method of claim 14, wherein the cell is in vivo.

16. The method of claim 14, wherein the cell is ex vivo.

17. The method of claim 14, wherein the cell is a hepatocyte.

18. The method of claim 14, wherein the cell is mammalian.

19. The method of claim 14, wherein the cell is human.

* * * * *

UNITED STATES PATENT AND TRADEMARK OFFICE
CERTIFICATE OF CORRECTION

| | | |
|---|---|---|
| PATENT NO. | : 9,994,600 B2 | Page 1 of 4 |
| APPLICATION NO. | : 15/323080 | |
| DATED | : June 12, 2018 | |
| INVENTOR(S) | : Lin Zhi | |

It is certified that error appears in the above-identified patent and that said Letters Patent is hereby corrected as shown below:

On the Title Page

Item (54), Title, at Line 2, Change "THEROF" to --THEREOF--.

In Column 1, Notice, at Line 3, After "0 days." delete "days.".

In Column 2, (Item (56)), at Line 45 (Approx.), Under Other Publications, change "nd" to --and--.

In Column 2, Page 3 (Item (56)), at Line 34 (Approx.), Under Other Publications, change "Diphosphabicycle" to --Diphosphabicyclo--.

In Column 1, Page 4 (Item (56)), at Line 33, Under Other Publications, change "Antagonist,"" to --Antagonists,"--.

In Column 2, Page 4 (Item (56)), at Line 1, Under Other Publications, change "2'C-Methylnucleosides" to --2'-C-Methylnucleosides--.

In Column 2, Page 4 (Item (56)), at Line 10, Under Other Publications, change ""3-mehtyl" to --"3-methyl--.

In Column 2, Page 5 (Item (56)), at Line 5, Under Other Publications, change "oxoguinoline" to --oxoquinoline--.

In Column 1, Page 6 (Item (56)), at Line 34, Under Other Publications, change "1.3,21ambd5-" to --1.3,2lambd5- --.

In Column 2, Page 6 (Item (56)), at Lines 25-26, Under Other Publications, change "dioxaphosphorinan 2 yl]2'" to --dioxaphosphorinan-2-yl]-2'--.

Signed and Sealed this
Sixteenth Day of April, 2019

Andrei Iancu
*Director of the United States Patent and Trademark Office*

CERTIFICATE OF CORRECTION (continued)
U.S. Pat. No. 9,994,600 B2

In Column 1, Page 7 (Item (56)), at Line 41 (Approx.), Under Other Publications, change "iota-Menthane,"" to --iota-Menthone,"--.

In Column 2, Page 7 (Item (56)), at Line 23, Under Other Publications, change "3-Alkenoyl" to --3-Alkenoyl--.

In Column 2, Page 7 (Item (56)), at Line 38, Under Other Publications, change "Hydroxymethyl" to --Hydroxymethyl--.

In Column 2, Page 8 (Item (56)), at Line 9, Under Other Publications, change "AASALD" to --AASLD--.

In Column 2, Page 8 (Item (56)), at Line 65 (Approx.), Under Other Publications, change "AASALD" to --AASLD--.

In Column 1, Page 10 (Item (56)), at Line 60 (Approx.), Under Other Publications, change "HepDirect"" to --HepDirect™--.

In Column 2, Page 10 (Item (56)), at Line 37, Under Other Publications, change "5-bromo-4-fenil" to --5-bromo-4-fenil--.

In Column 1, Page 11 (Item (56)), at Line 9, Under Other Publications, change "Capecitabind"" to --Capecitabine"--.

In Column 1, Page 11 (Item (56)), at Line 57 (Approx.), Under Other Publications, change "AASALD" to --AASLD--.

In Column 2, Page 11 (Item (56)), at Line 46 (Approx.), Under Other Publications, change "3" to --J--.

In Column 2, Page 12 (Item (56)), at Line 51 (Approx.), Under Other Publications, change "coliinn" to --coli In--.

In the Specification

In Column 1 at Line 2, Change "THEROF" to --THEREOF--.

In Column 2 at Line 37, Change "hereroalkyl," to --heteroalkyl,--.

In Column 3 at Line 1, Change "hereroalkyl," to --heteroalkyl,--.

In Column 3 at Line 34 (Approx.), Change "hereroalkyl," to --heteroalkyl,--.

In Column 3 at Line 47, Change "NW$^3$;" to --NR$^3$;--.

In Column 4 at Line 4 (Approx.), Change "hereroalkyl," to --heteroalkyl,--.

CERTIFICATE OF CORRECTION (continued)
U.S. Pat. No. 9,994,600 B2

In Column 4 at Line 43 (Approx.), Change "EASL," to --EASL--.

In Column 6 at Line 59 (Approx.), Change "hereroalkyl," to --heteroalkyl,--.

In Column 6 at Line 60, Change "$C_7$-$C_6$" to --$C_2$-$C_6$--.

In Column 7 at Line 67, Change "diphosphate." to --triphosphate.--.

In Column 9 at Line 11, Change "human," to --human.--.

In Column 10 at Line 6, Change "acylaminoalkyl," to --alkylaminoalkyl,--.

In Column 10 at Line 50, Change ""alkenyl"" to --"alkynyl"--.

In Column 10 at Line 54, Change "alkenyl" to --alkynyl--.

In Column 11 at Line 18, Change "$G_{3-8}$" to --$C_{3-8}$--.

In Column 11 at Lines 28-29, Change "alkylsulfinyl alkylsulfonyl," to --alkylsulfinyl, alkylsulfonyl,--.

In Column 11 at Line 41, Change "$C_{1-6}$alkyl," to --$C_{1-6}$-alkyl,--.

In Column 11 at Line 54, Change "I, III and IV" to --I, II, III and IV--.

In Column 11 at Line 58, Change "(+)-7,7dimethyl" to --(+)-7,7-dimethyl--.

In Column 12 at Line 2, Change "terphthalic" to --terephthalic--.

In Column 12 at Line 15 (Approx.), Change "human," to --human.--.

In Column 12 at Line 24 (Approx.), Change "hut" to --but--.

In Column 12 at Line 35 (Approx.), Change "compound in" to --compound. In--.

In Column 12 at Line 37, Change "unproved" to --improved--.

In Column 12 at Line 39, Change "he" to --be--.

In Column 12 at Line 61, Change "points," to --points.--.

In Column 12 at Line 66, Change "7,666.855," to --7,666,855,--.

In Column 13 at Line 8, Change "drug," to --drug)--.

In Column 13 at Lines 53-54, Change "terphthalate," to --terephthalate--.

CERTIFICATE OF CORRECTION (continued)
U.S. Pat. No. 9,994,600 B2

In Column 16 at Line 16, Change "H." to --II.--.

In Column 17 at Line 29 (Approx.), Change "Formula. IV." to --Formula IV.--.

In Column 19 at Line 32 (Approx.), Change "0° C. In" to --0° C. in--.

In Column 19 at Line 67, Change "2.95.15." to --295.15.--.

In Column 20 at Line 1, Change "1H )," to --1H),--.

In Column 20 at Line 9 (Approx.), Change "[3.1.1]nonane" to --[3.3.1]nonane--.

In the Claims

In Column 21 at Line 45 (Approx.), In Claim 5, after "compound" insert --of--.